United States Patent [19]

Palmer et al.

[11] Patent Number: 5,126,247
[45] Date of Patent: Jun. 30, 1992

[54] METHOD, SYSTEM AND DEVICES FOR THE ASSAY AND DETECTION OF BIOCHEMICAL MOLECULES

[75] Inventors: John L. Palmer, Philadelphia; James B. Johnston, Ambler; Marsha W. Timmerman, Allentown, all of Pa.

[73] Assignee: Enzymatics, Inc., Horsham, Pa.

[21] Appl. No.: 160,595

[22] Filed: Feb. 26, 1988

[51] Int. Cl.⁵ .......................... C12Q 1/26; C12M 1/40
[52] U.S. Cl. .................................... 435/25; 435/4; 435/26; 435/175; 435/174; 435/805; 435/810; 435/288; 435/292; 435/294
[58] Field of Search .................... 435/4, 25, 26, 175, 435/176, 177, 178, 179, 805, 810, 288, 292, 293, 294, 295, 296; 606/181

[56] References Cited

U.S. PATENT DOCUMENTS

| | | | |
|---|---|---|---|
| 3,964,871 | 6/1976 | Hochstrasser | 23/253 |
| 4,556,634 | 3/1985 | Misaki et al. | 435/25 |
| 4,629,697 | 12/1986 | Limbach et al. | 435/26 |
| 4,761,381 | 8/1988 | Blatt et al. | |

FOREIGN PATENT DOCUMENTS 0117032  6/1984  European Pat. Off. .

Primary Examiner—Esther L. Kepplinger
Assistant Examiner—Toni R. Scheiner
Attorney, Agent, or Firm—Finnegan, Henderson, Farabow, Garrett & Dunner

[57] ABSTRACT

Oxygen-independent methods, systems and devices for the enzymatic colorimetric assay and detection of biochemical analytes. Two systems are described, both of which produce less than one equivalent of dye per equivalent of substrate, maintaining dye concentrations in the range where Beer's law predicts a linear color-concentration relationship. One system produces an analog color signal from an analog analyte input, the other system produces a digital color signal from an analog analyte input.

61 Claims, 1 Drawing Sheet

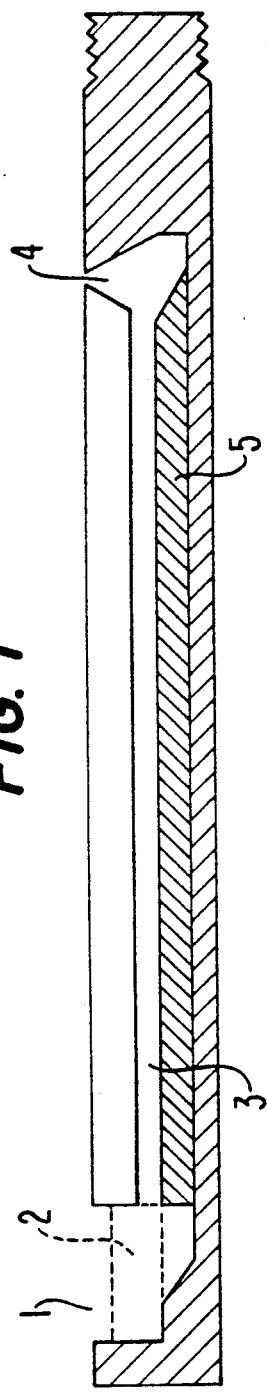
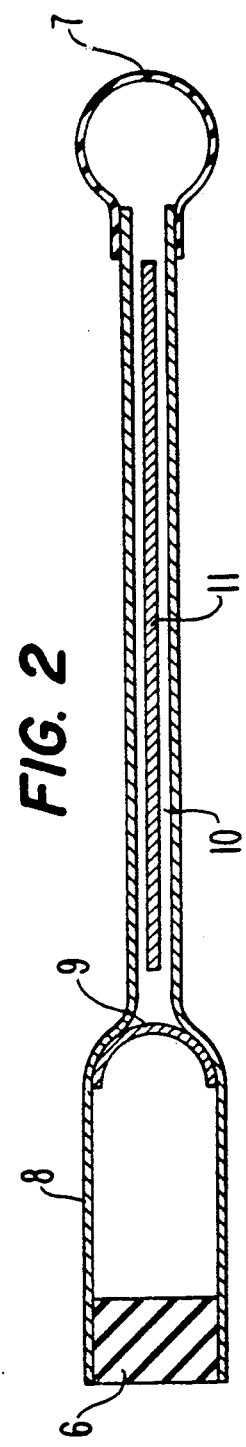
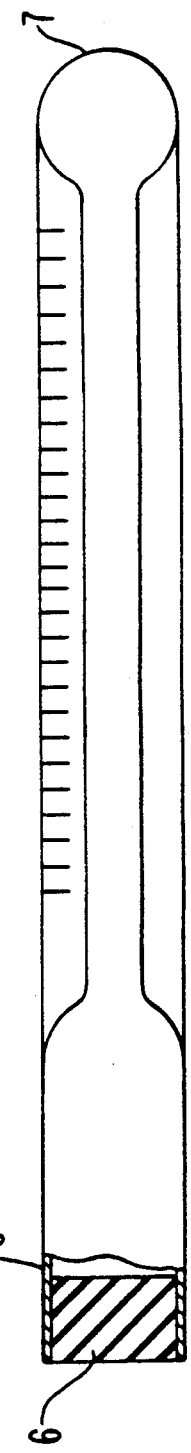
FIG. 1
FIG. 2
FIG. 3

METHOD, SYSTEM AND DEVICES FOR THE ASSAY AND DETECTION OF BIOCHEMICAL MOLECULES

BACKGROUND OF THE INVENTION

1. Field of the Invention

The invention relates to a novel system, devices and method for the enzymatic assay and detection of biochemical analytes. For convenience, the novel system, devices and method will often be referred to in a generic manner, as "systems". In the system of the invention, an analyte is reacted with an electron transferase enzyme, reducing the enzyme. The reduced enzyme is colorimetrically assayed as a means of determining the concentration or the presence (or absence) of the analyte.

The invention has several embodiments which will be described hereinafter. In one embodiment, the invention relates to systems which take an analog analyte concentration input and convert it to an analog colorimetric output signal. In these systems, there is a linear relationship between the analog analyte concentration input and the analog colorimetric signal.

In another embodiment, the invention relates to a system which takes an analog analyte concentration input and converts it to a digital colorimetric output signal. In this system, there is a digital colorimetric "off-on" signal corresponding to a sought level of the analog analyte concentration input, i.e., an analog to digital system. When the analyte is below the preselected threshold concentration, no visible color change occurs; when the analyte is at or above the preselected threshold concentration, a visible color change occurs. Therefore, in the analog to digital system, there can be determined the absence or presence of the analyte in the concentration to be determined.

While there are numerous novel and unobvious embodiments of the invention (which will be described in detail hereinafter), it can be noted at the outset, that insofar as could be determined from the search of the prior art, there appears to be no system that is operative or is based on an electron transferase enzyme which is capable of analog to digital or, alternatively, analog to analog inputs and outputs.

For convenience, "analog to digital" shall be abbreviated herein as "a/d" and "analog to analog" as "a/a". Other abbreviations will be explained hereinafter.

The measurement of concentration of biochemical analytes has many applications and uses in biomedical, medical, diagnostic, industrial (e.g. genetic engineering) and numerous other fields of art as will become readily apparent to one of average skill-in-the-art to which the invention pertains. The invention provides a test of extreme or high sensitivity and accuracy and with great convenience.

The known and useable prior art methods for enzymatic analysis of the concentration of biological analytes use oxidase enzyme based aerobic reactions which proceed as follows:

Substrate + $O_2 \rightarrow$ Oxidized Substrate + $H_2O_2$

As demonstrated in the above reaction, the enzyme oxidizes the substrate by removing two electrons to form an oxidized substrate. These two electrons are then transferred to molecular oxygen to form hydrogen peroxide. In the scientific and patent literature, enzymes that catalyze this reaction are known as "oxidases" and the presence of this activity in a process is known as "oxidase activity".

In common practice, the hydrogen peroxide produced in this reaction is then reacted with an electron donating chromogen, for example, 4-aminoantipyrine, in the presence of peroxidase enzyme to form a dye. The amount of dye produced is then used as a measure of the amount of substrate that is oxidized.

Alternatively, this reaction may be monitored by the use of an oxygen electrode to measure oxygen consumption or the oxidized substrate can be directly measured, for example, by its absorbancy in the ultraviolet region.

A number of disadvantages exist with the prior art technology, the most serious of which is the requirement for molecular oxygen in the reaction. The concentration of dissolved oxygen in air saturated water is approximately 0.24 mM. This concentration is far below the concentration in bodily fluids of many medically important biological molecules. For example, alcohol at 0.1% is at a concentration of 21.7 mM, cholesterol at 200 mg/dl is approximately 5 mM, the physiological concentration of glucose is 5 mM and concentrations of up to 50 mM are encountered in diabetic disease. Therefore, in any device that quantitatively oxidizes a biological molecule, the bodily fluid must be diluted to at least less than the concentration of oxygen in a bodily fluid, i.e., about 0.24 mM, before being measured. Without such dilution, a false reading would be obtained indicative of the concentration of oxygen, not of the medically important biological molecule.

Another reason leads to the requirement for dilution of the biological fluid when the oxidase reaction as is known in the prior art, is coupled to dye production. One molecule of hydrogen peroxide is produced for every molecule of substrate oxidized, and one molecule of dye is produced for every molecule of hydrogen peroxide.

Therefore, in a system that substantially completely oxidizes the substrate, the dye concentration would be at or greater than 5 mM for the medically important biological molecules listed above. Dye-dye interactions will occur at these high concentrations, and the amount of color in the solution will not be linearly proportional to the concentration of dye. Therefore, any device that measures the amount of color in the solution would not be able to determine the concentration of substrate that was oxidized. Therefore, in the prior art, the two above-discussed problems required that the analyte be diluted prior to use. There are other drawbacks to the methods and systems of the prior art.

In view of the problems of the prior art, there exists a real need for a system, methods, and devices for the enzymatic assay and detection of biochemical analytes which do not have the aforementioned disadvantages.

In view of the problems associated with the oxygen concentration in biological fluids described above, there exists a particularly serious need for an accurate analytical system in which oxygen presents no limiting factor in the reaction. As described in greater detail hereinafter, the system (and the process) of the invention is independent of oxygen in the analyte; i.e., the system of the invention is operative regardless of whether or not oxygen is present. Indeed, the system is capable of operating in the absence of oxygen, but oxygen can also be present. This is one of the distinctive features of the invention. Oxygen is not used in the reaction of the invention, as further described herein.

2. Objects and Features of the Invention

The present invention provides a pioneering departure from the prior art for the assay and detection of various biochemical analytes which substantially obviates the disadvantages of the oxidase enzyme systems of the prior art.

The invention provides a system, a method and devices which have numerous practical applications and contribute to the advancement of technology in the fields to which this invention applies. The invention provides an accurate, precise, fast and reliable system, method and devices, hereinafter "system", for the enzymatic assay and detection of biochemical analytes.

The invention described allows for the assay and detection of the biochemical analytes without dilution in easy to use, disposable diagnostic devices. The invention provides a system wherein molecular oxygen is not involved in the process described and oxidase enzyme activity is not utilized. Therefore, the concentration of biological molecule assayed is not limited by the concentration of dissolved oxygen.

Furthermore, in the invention, there is produced less than one equivalent of dye per equivalent of substrate. Therefore, dye concentrations are always in the range where Beer's law predicts a linear color-concentration relationship.

Thus, the invention provides a solution to both of the problems described above, and there is no need to dilute the analyte prior to use, or at any time thereafter.

In one embodiment, the invention provides an analog to analog colorimetric signal system, wherein an analog color signal is produced from an analog analyte concentration input. The signal has a unique characteristic, namely the signal is always produced with less than one equivalence of dye per equivalence of input. In this manner, the "gain" of the color signal is limited to a region where Beer's law predicts a linear color-concentration relationship. Therefore, in the system of the invention, the concentration of the analyte is ascertainable linearly over a preselected range.

In another embodiment of the invention, there is provided an analog to digital colorimetric signal system, wherein a digital color signal is produced from an analog analyte concentration input. This device does not require the subjective matching of color intensity to a color chart, or the use of a colorimeter to determine the concentration of analyte. Thus, this embodiment of the invention also has distinct advantages over the prior art.

With respect to "reactive components" of the system of the invention, (which components will be described in further detail herein below), the invention also has distinctive features. Certain of the aspects of the two embodiments of the invention described above (the "a/d" and the "a/a" embodiments) call for a multiplicity of reactive components; in other aspects, the components are "multi-functional" reactive components. Thus, in the systems which use "multi-functional" components, i.e., components which perform or are capable of performing more than one function, a smaller number of components are needed. In the systems which use components which are capable of performing one function only, more components, each performing a different function, are needed.

The capability of the system of the invention to perform with a few selected components, or with a larger number of reactive components, is yet another advantageous feature of the invention.

Thus, an important object of the invention is to provide an accurate and versatile analytical system, method and devices for the assay of biochemical analytes which is operative without the necessity o diluting the biological material to be analyzed and is operative without oxygen, or, i.e., does not depend on oxygen.

While one embodiment of this invention assays biochemical analytes by measuring the activity of the analyte with an electron transferase enzyme, this invention can also be utilized to assay electron transferase enzymes and other oxidizing compounds by measuring the activity of the electron transferase enzyme or other oxidizing compound with a reductive compound.

Therefore, another important object of the invention is to provide an analytical system, method and devices for the assay of electron transferase enzymes and other biochemical oxidizing compounds.

The listing of objectives provided herein—or of the features of the invention—is not intended to be exhaustive, but merely illustrative.

Other objects will become apparent to one of average skill-in-the-art in the further description of the invention.

3. Brief Description of the Prior Art

Typical of the conventional, oxygen-dependent, colorimetric oxidase diagnostic technology are the following issued patents:

U.S. Pat. No. 4,166,763 describes a multi-layer analytical device for the detection of lactate using lactate oxidase. In this patent, the lactate is oxidized to pyruvate by lactate oxidase in an oxygen-dependent manner to produce hydrogen peroxide. The hydrogen peroxide is detected by oxidation of a chromogen colorimetrically using peroxidase catalyzed detection.

U.S. Pat. No. 3,886,045 and Re. 29,498 describe a system for the assay of glucose involving glucose oxidase and peroxidase. In these patents, glucose oxidase catalyzes the oxygen-dependent oxidation of glucose to produce hydrogen peroxide. In contrast to the patent discussed above, the hydrogen peroxide does not react directly with an electron-donating chromogen to produce a dye. Instead, the hydrogen peroxide is reduced to water with the concomitant oxidation of ferrocyanide in a peroxidase catalyzed reaction. The ferricyanide produced then reacts with electron donating chromogen to produce dye in an uncatalyzed reaction.

U.S. Pat. No. 4,288,541 discloses a method to reduce the interfering effects of reducing agents on the analysis of a component in a liquid test solution which contains such interfering substance. The patent discloses that the addition of water-soluble mercuric ions bound to organic ligands renders a hydrogen peroxide/peroxidase colorimetric system insensitive to the presence of ascorbate in the test sample. Without this improvement, ascorbate will react with and destroy the hydrogen peroxide produced by an oxidase and result in error.

U.S. Pat. No. 4,642,286 describes a composition and method for ethanol determination. The patent describes the use of alcohol oxidase to catalyze the oxygen-dependent oxidation of alcohol to produce hydrogen peroxide and peroxidase to catalyze the hydrogen peroxide-dependent conversion of an electron donating chromogen to a dye.

PCT Patent Application Publication WO 85/01747 describes a device that contains an oxidase that reacts with a substrate to produce hydrogen peroxide, a compensator that will over a period of time react with and inactivate the oxidase, a reducing agent that will react with and destroy the hydrogen peroxide, a chromogen that will also react with the hydrogen peroxide when the reducing agent is depleted, and peroxidase to catalyze the reactions involving hydrogen peroxide. The method and devices described are capable of producing a digital on/off color signal in response to differing concentrations of analyte. However, this is significantly different from the invention described herein. Molecular oxygen is involved in the described reaction, limiting the concentration of substrate that is oxidized, as was discussed above herein. The patent describes the use of a first catalyst, an enzyme to produce a detectable reaction product. A compensator is supplied to inhibit the enzyme. In another described aspect, a second catalyst is provided to produce a product to facilitate detection, and in that aspect, the compensator inhibits the second catalyst. The compensator inactivates the oxidase after a set and predetermined time, so that the amount of substrate oxidized in this set time is measured. Thus, the work described by this WO 85/01747 publication measures substrate concentration by the rate of an enzyme reaction.

In accordance with the present invention, no compensator is utilized, hydrogen peroxide is not involved as an intermediate, and no reducing agent capable of reacting with and destroying hydrogen peroxide is employed. The measurement accuracy of the present invention is not time-dependent.

U.S. Pat. Nos. 3,964,871 and 4,059,407 are described to be useful for the measurements of ketones, proteins like albumin, uric acid or glucose in biological fluids. The patents disclose a device that contains different measuring regions, the differing regions turning color in a digital, on/off manner at different concentrations of the biological molecules like the glucose. The device described includes an oxidase which catalyzes the oxygen-dependent oxidation of substrate to produce hydrogen peroxide, a reducing agent that reacts with and destroys the hydrogen peroxide produced, a chromogen that reacts with the hydrogen peroxide when the reducing agent is depleted to produce a color, and peroxidase to catalyze the hydrogen peroxide-dependent reactions. In these patents, hydrogen peroxide is, as in the prior discussed patents, a required intermediate in the chemical reaction disclosed. This is in contrast to the invention disclosed herein.

U.S. Pat. No. 4,545,382 describes a sensor for detection of components of a liquid mixture. The device utilizes the electrons produced by an enzyme-analyte reaction to generate an electric current on an electrode, the intensity of which is a function of analyte concentration. The system described requires a sensor and the sensor described in the patent is useful only when connected to a sensitive and expensive current measuring meter. The patent does not describe the use of a colorimetric system to determine analyte concentration, as in the present invention.

U.S. Pat. No. 3,925,164 describes a method for determining cholesterol (total or bound) with cholesterol esterase and then measuring the resulting quantity of total cholesterol using various standard determinations, for instance, an oxygen-dependent cholesterol oxidase method in which hydrogen peroxide is a necessary intermediate. In one disclosed procedure, the oxygen consumption, the $H_2O_2$ formation or formation of cholestenone are measured. The process described is dependent on oxygen consumption and formation of $H_2O_2$. This is, as described above, different from the present invention.

U.S. Pat. No. 3,884,764 describes a method for the measurement of total cholesterol in serum comprising cholesterol oxidase, a protease, and a lipase having cholesterol esterase activity. In that method, the lipase and protease break down esterified cholesterol, liberating free cholesterol. Cholesterol oxidase catalyzes the oxidation of free cholesterol to produce hydrogen peroxide. Peroxidase then catalyzes the reaction of hydrogen peroxide with an electron donating chromogen to produce a dye. A feature of the method is the use of the mixture of lipase (having cholesterol esterase activity) and protease in place of cholesterol esterase. The other aspects of the patent utilize traditional technology, i.e., the reaction is oxygen-dependent and hydrogen peroxide is a critical intermediate in the measurement.

U.S. Pat. No. 4,212,938 describes an oxygen-dependent method for the assay of cholesterol in an aqueous medium. The assay involves incubating the sample with cholesterol oxidase and determining either the oxygen consumption, the hydrogen peroxide formed or the amount of cholestenone (oxidized cholesterol) produced as a measure of the initial cholesterol content. Here again, this is an oxygen-dependent reaction and $H_2O_2$ is produced.

U.S. Pat. No. 4,184,921 also describes an oxygen-dependent process and reagent for determining cholesterol. The method calls for cholesterol esterase, cholesterol oxidase, peroxidase, 4-aminophenazone, a surface active agent and phenol. In the method, the hydrogen peroxide formed by the cholesterol oxidase is used to oxidize the phenol in a peroxidase-catalyzed reaction. The oxidized phenol in turn reacts with the 4-aminophenazone to form a dye. Again, in this method, hydrogen peroxide is a necessary intermediate in the measurement of cholesterol.

U.S. Pat. No. 3,907,645 describes an oxygen-dependent cholesterol assay using an enzyme that converts cholesterol to delta 4-cholestenone and hydrogen peroxide. The patent describes methods for determining cholesterol concentration by reacting a cholesterol-containing solution with a base to free any bound cholesterol, reacting the free cholesterol with cholesterol oxidase in the presence of oxygen to form 4-cholestenone and hydrogen peroxide, and measuring either the hydrogen peroxide or the 4-cholestenone to determine the amount of cholesterol present in the initial sample.

The oxygen-dependent oxidase enzyme systems, methods and devices of the earlier patents are significantly different from and have serious disadvantages in comparison with the system, method and device of the invention described herein. None of the earlier patents describe devices in which less chromogen is produced than substrate oxidized. And the earlier patents all describe assays in which the reaction is dependent upon and limited by the concentration of oxygen in the analyte fluid. Both of these shortcomings require dilution of the analyte sample, and have the other undesirable qualities discussed above. The present invention contributes a solution to these troublesome problems.

Moreover, this review of the prior art shows that for a period of over ten years, the enzymatic assay of biological molecules in biological media has been based upon oxygen-dependent reactive systems, demonstrating that the present invention is that much more unexpected.

4. Related Patent Applications

The following co-pending patent applications relate to enzymatic assays and detection of biochemical analytes.

Patent application Ser. No. 942,414, filed Dec. 16, 1986 and Ser. No. 075,817, filed Jul. 20, 1987 describe dehydrogenase enzyme systems for the assay and detection of biological analytes. Patent application Ser. No. 106,745, filed Oct. 9, 1987, describes an oxygen-dependent oxidase enzyme system for the assay and detection of biological analytes for which hydrogen peroxide is a necessary intermediate.

The above three applications describe analog to analog systems in which the "gain" of the color signal is reduced and analog to digital systems in which a digital color signal is produced from an analog analyte concentration input.

SUMMARY OF THE INVENTION

The invention comprises a method for the measurement of biochemical analytes. The method comprises reacting the analyte, the concentration or presence of which is to be measured, with an enzyme capable of electron transferase activity with the analyte, thus resulting in reduced enzyme. The enzyme is colorimetrically assayed to determine the concentration or presence of the analyte. In accordance with the invention, the enzyme reaction proceeds under conditions which are not oxygen-dependent.

In accordance with the invention, there are two colorimetric assay systems by which the reduced enzyme, the amount of which corresponds to the analyte concentration, may be colorimetrically assayed. One system produces an analog color signal from an analog analyte concentration input. The other produces a digital signal from an analog analyte concentration input. As will be discussed below, whether a colorimetric assay system is analog to analog (a/a) or analog to digital (a/d) will depend upon the selection of components. Therefore, unless otherwise specified, the term colorimetric assay system refers to both analog to analog and analog to digital systems.

In the analog to analog system, the electron acceptor and chromogen share the ability to be repositories of electrons in order that electrons may be proportionally divided among the chromogen and electron acceptor. Thus, (as described further below) the accumulation of reduced chromogen is maintained at a level at which the analyte concentration to chromogen color relationship is linear. The analog to analog system requires separate electron acceptor and chromogen components to serve as co-repositories of electrons.

In the analog to digital system, the chromogen does not undergo reduction and no color change occurs, unless a predetermined threshold quantity of analyte is present, then the chromogen is reduced and a color change takes place which signals a concentration of analyte equal to or greater than the threshold concentration. For this change in color to occur, reduction of the chromogen should not occur to any significant extent until the threshold concentration of analyte is consumed. This is accomplished in accordance with the invention by having the electron acceptor preferentially accept electrons from the reduced enzyme and prevent the accumulation of reduced chromogen until the threshold concentration of electron acceptor and, hence, analyte, is consumed. At this threshold, reduced chromogen accumulates and a color change occurs when reduced enzyme is present. In the absence of reduced enzyme, reduced chromogen does not accumulate, and no color change occurs. The threshold concentration level is controlled by using a predetermined quantity of electron acceptor, corresponding to the desired threshold concentration of analyte.

In both the analog to analog and analog to digital systems, it is necessary that the electron transfer to the electron acceptor be functionally irreversible; the electron transfer to the chromogen may also be irreversible. It should be noted that the systems of the present invention are dynamic chemical equilibrium reactions, the states of which at any given time cannot be described in absolute terms. See Peters, et al, *Chemical Separations and Measurements*, pp. 58-59 (W. B. Saunders, Philadelphia 1974). A functionally irreversible equilibrium state between the enzyme and the electron acceptor is one in which essentially all of the electron acceptor is reduced and essentially all of a proportionally equivalent quantity of enzyme (depending upon the number of electrons accepted by an electron acceptor molecule) is non-reduced. However, because equilibrium systems are dynamic and not static, even those systems satisfying the above definition will contain quantities of non-reduced electron acceptor in the presence of reduced enzyme. Those skilled in the art will choose system components that will minimize the accumulation of non-reduced electron acceptor when reduced enzyme is present.

In accordance with the invention, therefore, the colorimetric assay system comprises an enzyme and one or more components to promote the reaction and to determine the extent to which the reduced enzyme has been produced by reaction with the analyte.

In the description of the invention, certain terms will be used which are defined further below. The definitions are supplemented by the description throughout the specification.

Enzyme (enz.)—A compound capable of electron transferase activity with the analyte, one molecule of which is capable of removing two electrons from the analyte molecule, resulting in reduced enz.

Electron Acceptor (ea)—A compound of larger reduction potential than the reduced enzyme, which functions as an electron "sink" and is capable of irreversibly accepting electrons transferred from the enzyme, accumulating electrons so that there is always produced less than one equivalent of chromogen per equivalent of analyte oxidized.

Chromogen (chr.)—A compound which is capable of accepting electrons transferred from the enzyme and capable of changing color in the visible range upon reduction.

Electron Transfer Agent (eta or e/t/a)—A compound capable of promoting the transfer of electrons from the enz. to either the ea, the chr, or both. The eta is also capable of promoting the transfer of electrons between the reduced ea and the chr, and vice-versa.

In the description, the term "reaction not oxygen-dependent" is used, or the enzyme is described as being "capable of removing electrons in the absence of oxygen."

In accordance with the invention, the system comprises an electron acceptor of larger reduction potential than the reduced enzyme, which functions as an electron sink and is capable of accepting one or more electrons transferred from the enzyme. The electron acceptor accumulates electrons in a functionally irreversible manner in order that there always is produced less than one equivalent of reduced chromogen per equivalent of analyte oxidized, thereby maintaining dye concentrations in the range where Beer's law predicts a linear color-analyte concentration relationship. As will be disclosed herein below, a class of electron acceptors are capable of changing color upon reduction and are not utilized in combination with a chromogen. Such compounds therefore need not be used to prevent the accumulation of reduced chromogen.

Further, the system comprises a chromogen, which is capable of accepting one or more electrons transferred from the enzyme and which is capable of changing color in the visible range upon reduction. Chromogens are used when electron acceptors are incapable of changing color upon reduction as described above, or when the color change by the electron acceptor is not desired and a color change by a chromogen is preferable. In the system of the invention, the chromogen may be colorless to start with and develop a color upon reduction, or the chromogen may be colored to start with and become colorless as the reaction is completed or the chromogen may be a light color and change to a deep or other distinctive color.

Accordingly, a "color change" generally refers to each of these described features. One skilled in the art can readily select from known chromogens those (or that) particular one(s) best suited for the purpose sought to be achieved under the particular circumstances, such as the particular analyte, the concentration of which is to be measured and the visible spectrum in which the color change is expected to occur.

Further, the system comprises an electron transfer agent which is capable of promoting the transfer of one or more electrons from the enzyme to the electron acceptor, to the chromogen or to both, when either or both are incapable of efficiently removing electrons directly from the reduced enzyme. A component is defined as inefficient if the rate at which it directly removes electrons from the enzyme is too slow to allow the production of a commercially viable product at a reasonable cost.

A slow system reaction rate can render a product commercially non-viable. Slow electron transfer between the reduced enzyme and other components can be compensated for by increasing the quantity of enzyme. However, enzymes are the most expensive component of the present invention and the quantity of enzyme required to increase the system reaction rate to a commercially viable speed in many cases results in a product that is prohibitively expensive.

The inefficiency of a product component can be remedied by adding an electron transfer agent to the system, which is a more economical component than the enzyme. This eliminates both the slow reaction rate and prohibitive cost of a system with an inefficient component.

An inefficient component is also defined as being functionally incapable of directly removing electrons from the reduced enzyme. In the dynamic equilibrium reactions of the systems of the present invention, a component cannot be described as absolutely incapable of directly removing electrons from the reduced enzyme. However, a component is described as functionally incapable if it is unable to directly remove electrons from the reduced enzyme in a commercially viable quantity or rate.

The route of the electrons from the analyte to the electron acceptor is not important to the performance of the invention except that the enzyme must be involved in at least one step in this route. The presence or absence of any of the above-described components or the routes taken by electrons between components is of no consequence to the invention described herein. In most systems, more than one of the illustrated pathways are occurring simultaneously. The pathways generally do not predominate for any given combination of system components. The presentation made hereinbelow is not intended to limit or commit the invention to any specific theory or hypothesis. Possible routes for electron movement include, but are not limited to, those presented graphically below.

In the schematic illustrations shown below, the arrows indicate alternate routes for the electrons. For illustrative purposes only, the components, that is, the "e/t/a," the "e/a" and the "chr" are shown as separate or individual components (the "e/t/a" being referred to as "Transfer Agent"). As described herein, however, a compound may be multi-functional, that is, it serves several functions. An illustration of a multi-functional component which serves or operates as transfer agent, electron acceptor and chromogen is seen in illustrations 4 and 6. In illustration 7, the transfer agent serves also as chromogen. In illustration 8, the transfer agent serves also as electron acceptor.

Illustration 6 is the same illustration as illustration 4, save that the electron acceptor has been re-named to illustrate its multi-functional properties. The same electron acceptor compounds that function in illustration 4 also function in illustration 6. No additional electron acceptor compounds function in illustration 6 that do not function in illustration 4 and there are no additional electron acceptor compounds that function in illustration 4 that fail to function in illustration 6. The electron acceptor in illustration 6 is the same electron acceptor as in illustration 4. It is additionally described as a chromogen because the compound changes color upon reduction, obviating the need for a separate chromogen component. The electron acceptor is also described as an electron transfer agent because it is capable of directly and efficiently removing electrons from the reduced enzyme, obviating the need for a separate electron transfer agent component. However, unlike the separate electron transfer agent components of the other illustrations, the electron transfer agents of this illustration do not transfer electrons from one component to another.

Likewise, illustration 7 and 8 are the same embodiment as illustration 1. In both cases, components have been re-named to illustrate their multi-functional properties.

1)

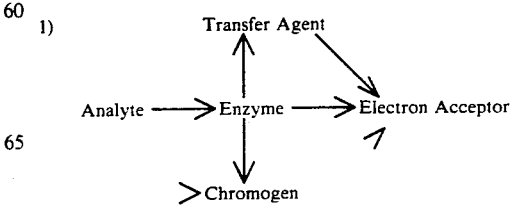

-continued

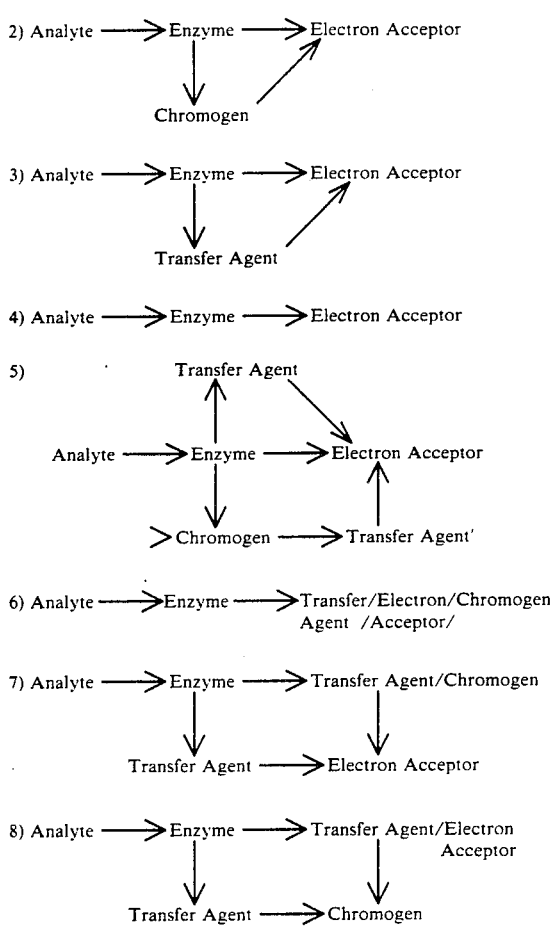

The schematics shown illustrate the versatility of the invention.

In illustration 1 in addition to the enzyme, the colorimetric assay system comprises an electron acceptor, a chromogen and an electron transfer agent for promoting the transfer of one or more electrons from the enzyme to either the chromogen, the electron acceptor, or both. Illustration 1 shows the multiple electron pathways that can exist simultaneously in a system comprising these elements. Illustration 7 and 8 are the same as illustration 1, except that in illustration 7 the chromogen is capable of efficient direct interaction with the enzyme without the use of electron transfer agent, and has been re-named transfer agent/chromogen to illustrate this feature, and in illustration 8 the electron acceptor is capable of efficient direct interaction with the enzyme without the use of electron transfer agent and has been re-named transfer agent/electron acceptor to illustrate this feature. Typical of illustrations 1, 7 and 8 is a system for the analog to digital colorimetric measurement of cholesterol in which cholesterol electron transferase is the enzyme, 3,5-diphenyl tetrazolium bromide (MTT) is the chromogen, phenazine methosulfate (PMS) is the electron transfer agent and ferricyanide is the electron acceptor. An analog to analog version of this system for the colorimetric assay of bilirubin can be prepared by substituting bilirubin electron transferase for cholesterol electron transferase and tetrafluoro-1,4 benzoquinone (TFBQ) for ferricyanide.

When both the chromogen and electron acceptor are capable of efficient direct interaction with the enzyme, the colorimetric assay system comprises, in addition to the enzyme, a chromogen and an electron acceptor, such as in illustration 2. Typical of illustration 2 is a system for the analog to digital colorimetric measurement of glucose in which glucose electron transferase is the enzyme, MTT is the chromogen, and phenothiazine (PT) radical cation is the electron acceptor. An analog to analog version of this illustration, for the colorimetric assay of glucose, can be devised by substituting tartrazine (TAR) as the electron acceptor.

When the electron acceptor is capable of changing color upon reduction, the colorimetric assay system comprises in addition to the enzyme, an electron acceptor and electron transfer agent, as in illustration 3. When the electron acceptor capable of changing color upon reduction, is also capable of efficient direct interaction with the enzyme, the colorimetric assay system comprises the electron acceptor, in addition to the enzyme, as in illustration 4. Because a separate chromogen component is not used in illustrations 3 or 4, it is not possible to devise an analog to analog version of either illustration. It should also be noted that illustrations 3 and 4 of the invention depend upon the use of an electron acceptor with a high extinction coefficient for the color change of the electron acceptor to produce a threshold color change in the analog to digital system, as opposed to a system whereby electrons are prevented from reducing a color changing compound. Accordingly, unlike the other analog to digital systems, in which the proportion of reduced color changing molecule (chromogen) to oxidized analyte is less than one-to-one, the proportion of reduced color changing molecule (electron acceptor) to oxidized analyte is exactly one-to one.

Typical of illustration 3 is a system for the analog to digital colorimetric measurement of cholesterol, in which cholesterol electron transferase is the enzyme, Azure B is the electron acceptor, and 2,3-dimethoxy-5-methyl-1,4-benzoquinone (DMMBQ) is the electron transfer agent.

Illustration 4 is the same as illustration 6, in which the electron acceptor capable of efficient direct interaction with the enzyme and capable of changing color upon reduction has been designated as transfer agent/electron acceptor/chromogen to illustrate its multi-functional properties.

Typical of illustrations 4 and 6 is a system for the analog to digital colorimetric measurement of choline, in which choline electron transferase is the enzyme and Azure B is the electron acceptor.

The invention includes single phase and multi-phase systems, for example, when one phase is aqueous and the other is not. Commonly that phase can be a fatty or oily phase constituted for instance by triglycerides, and other non-aqueous constituents of body fluids.

It is often desirable, in such multi-phase systems, to provide a kinetic pathway between the electron acceptor and chromogen to enable the electron acceptor to remove electrons from reduced chromogen and prevent the premature accumulation of this material. A separate electron transfer agent serves as this kinetic pathway. There is then supplied a second electron transfer agent, as in illustration 5.

Typical of illustration 5 is a system for the analog to digital colorimetric measurement of serum glucose, in which glucose electron transferase is the enzyme, PT radical cation is the electron acceptor, DMMBQ is the electron transfer agent, nitro blue tetrazolium (NBT) is the chromogen, and TFBQ is the electron transfer agent between chromogen and electron acceptor.

An analog to analog version of this illustration, can be devised by substituting 2,3-dichloro-5,6-dicyano-1,4-benzoquinone (CCBQ) as the electron acceptor.

The devices of and the embodiment of the invention comprise the above system incorporated on a support member. Some devices of the invention comprise a plurality of regions with different concentrations of electron acceptor at different regions of the device, for example in a linear concentration gradient. The concentration of analyte then corresponds to the largest concentration of non-reduced electron acceptor completely reduced resulting in a color change. Other devices are described below.

The method of the invention comprises in a general manner, bringing the analyte, the concentration of which is to be determined, in contact with the reactant(s), including the enzyme(s) under such conditions as to cause a reaction, allowing the reaction to proceed and a color change to take place. Where no color change occurs in the a/d system, the concentration of the analyte is not present at concentrations at or above the threshold. In the a/a system, the color change is linearly related to the concentration of the analyte. Further description of the method follows hereinafter.

BRIEF DESCRIPTION OF THE DRAWINGS

FIG. 1 shows a diagnostic device for the machine independent determination of cholesterol concentrations in which the support member is a capillary tube, as described in Example 10 below.

FIG. 2 shows the side view of a similar diagnostic device in which the support member is a Vacutainer Blood Circulation Tube.

FIG. 3 shows a top view of the device of FIG. 2, in which the measuring grid is depicted.

DETAILED DESCRIPTION OF THE INVENTION

This invention is useful in the colorimetric enzymatic assay and detection of a great variety of biochemical analytes. There follows now a detailed description of the components (and their functions) of the system of the invention.

1. Detailed Description of the Enzyme

As has been referred to above, unlike the oxygen-dependent diagnostic systems of the prior art, molecular oxygen is not involved in the functioning of the electron transferase enzymes in the system of the present invention. Although many of the suitable enzymes are commonly known as "oxidases," it is not the classical oxidase reaction that is being utilized by this invention. The physiological reaction that these enzymes traditionally catalyze is the "oxidase" reaction, which involves the oxygen-dependent oxidation of analyte to produce hydrogen peroxide. However, in this invention, the enzymes are presented with non-physiological electron-accepting molecules and coerced to catalyze an unusual and non-physiological reaction. This unusual reaction then turns out to be highly advantageous because substrate concentration is no longer limited by the concentration of dissolved oxygen, as was described hereinabove.

An electron transferase enzyme is defined as an enzyme with the ability to take electrons directly from its corresponding substrate and transfer the electrons to an electron-accepting molecule that is not oxygen.

It is surprising in the present invention, that oxygen can be present among the reagent components but does not participate nor is needed in the reaction. Thus the system (the device) of the invention need not exclude air. Indeed, if oxygen did participate it would interfere with the system reaction and render it inaccurate. However, it has been determined that when oxygen is present, some of the electron transfer agents compete advantageously over it to oxidize the reduced enzyme.

The enzyme kinetics of the present invention differ significantly from that of the oxygen-dependent oxidase-based diagnostic systems of the prior art. In both systems, the analyte binds to the enzyme, which then catalyzes the removal of two electrons from the analyte, reducing the enzyme. In the prior art, a molecule of molecular oxygen then binds to the reduced enzyme, reoxidizes it and forms hydrogen peroxide, which then diffuses off the enzyme. In contrast in the present invention, either the electron acceptor, the chromogen, or when necessary, the electron transfer agent, binds to the reduced enzyme, reoxidizes it and diffuses off in reduced form. This mechanism is defined as electron transferase activity.

Enzymes of the class used herein have been studied and reported upon in the scientific literature. It has been found that most of the enzymes suitable for this invention contain a bound flavin coenzyme, although the presence of flavin coenzyme cannot be taken as a requirement for choice of enzyme. The mechanism of flavin containing enzymes is outlined in a review published by G. Palmer and V. Massey, *Biological Oxidations*, pp. 263–300 (Interscience Publishers, T. P. Singer, ed., New York 1968). Another class of enzymes that can be utilized in this invention are the copper containing oxidoreductases. Typical examples of this class of enzymes include serum monoamine oxidase, liver dopamine hydroxylase, hemocyanin, ceruloplasmin, laccase, uricase, phenolase, transsulfurase, cerebrocuprein, erythrocuprein, hepatocuprein, plastocyanin, and dopamine-2-hydroxylase.

In general, the list of possible enzymes that can be used in this invention is large, limited by the necessity that the enzyme be capable of removing electrons from an analyte in the absence of molecular oxygen. Other suitable enzymes include those that contain a pteridine cofactor, for example phenylalanine hydroxylase, those that contain heme prosthetic groups, including but not limited to liver aryl-4-hydroxylase, liver naphthalene hydroxylase, alkoxyaryl hydroxylase, arylalklamine hydroxylase, and the like and the steroid hydroxylase family, camphor hydroxylase and fatty acid desaturase.

Generally, the term "aryl" refers to an aromatic group having no more carbons than "naphthalene"; the term "alkyl" and the "alkyl" portion of "alkoxy" generally is not larger than six carbons, not uncommonly a lower alkyl.

Another useful class are those oxidative enzymes which contain non-heme iron as typified by fatty acid hydroxylase, and alkane hydroxylase. Yet another class contains a thiol or dithiol functionality at the enzyme reactive site, which undergoes reversible oxidation and reductions during enzyme turnover, e.g. diaphorase, fatty acid synthetase, and alpha-keto acid oxidase. Another class of enzymes having electron transferance activity is the general class of flavin containing oxidative enzymes (most of which are not oxidases). Examples of this class are dihydrofolate reductase, lipoamide dehydrogenase, dihydropteridine reductase, luciferase, NADH peroxidase, sarcosine dehydrogenase, NADP-nitrate reductase, acyl CoA dehydrogenase, and Methylophilus methlotrophus alcohol dehydrogenase, all commercially available from Sigma Chemical Company. Additional flavin containing enzymes include: succinate dehydrogenase, mitochondrial 1-glycerolphosphate dehydrogenase, mycobacteria lactate oxidative decarboxylase, pseudomonas L-lysine oxidative decarboxylase, imidazole monooxygenase, lysine monooxygenase, dihydroorotic dehydrogenase, sulfite reductase, NADH dehydrogenase, choline dehydrogenase, and D-lactate dehydrogenase.

Examples of all of these enzymes are discussed in detail in Mahler and Cordes, *Biological Chemistry* (First and Second Ed., Harper & Row, New York 1966).

All of the enzymes specifically listed above and all members of the classes of enzymes listed above which met the criteria of this invention and those that have equivalent functions can be interchangeably utilized in this invention and in the examples appended hereto, as is obvious to one of average skill-in-the-art.

Because of the wide variety of enzymes that were found to possess this surprising, novel activity, it was necessary to find a common pattern for predicting useful enzymes. It was noticed that all of the enzymes listed above contain a coenzyme or prostic group that does not normally exchange with the solvent during the physiological enzyme reaction, and is capable of undergoing a one or two electron reduction in the presence of substrate, but in the absence of any additional electron acceptor (including but not limited to molecular oxygen). This leads to a definition of the term "oxidative electron transferase" as any enzyme which is capable of 1) reacting with, and oxidizing a substrate in the absence of any added electron acceptor, and 2) transferring those electrons to a non-physiological electron acceptor. This electron acceptor, as will be disclosed more fully below, can serve as either an intermediate in the electron flow in the system or as the final electron acceptor, if said non-physiological electron acceptor has a greater half cell reduction potential (as defined in, for example, Mahler & Cordes, *Biological Chemistry* (1st Ed.), infra., page 207), in which case said electron acceptor acts as a terminal electron acceptor in this system, or said non-physiological electron acceptor has a reduction potential in the same range as the enzyme, in which case said non-physiological electron acceptor acts as an intermediate in the transfer of electrons in this system.

Generally, however, an enzyme is suitable for the system of the present invention, if, in a solution containing the enzyme's specific substrate and in the absence of any electron acceptor, the enzyme will undergo a change in visible or UV spectrum indicative of the removal of two electrons from the substrate and reduction of the enzyme. It is believed that all enzymes that show such a change can be suitably used in this invention. Oxidase enzymes capable of oxidizing a substrate to produce hydrogen peroxide, such as those listed in Barman, *Enzyme Handbook* (Springer-Verlag, New York 1968, Supplement 1974), are generally able to pass this test.

It should be noted here that although the capability of oxidizing a substrate and producing hydrogen peroxide is a property of an appropriate oxidase enzyme for use in the invention, the enzyme does not operate to produce hydrogen peroxide, as has been noted already hereinabove.

In accordance with the invention, a large number of oxidase enzymes are known that can be interchangeably used as electron transferase enzymes in this invention. Typical oxidases are the following commercially available oxidases or to be available oxidases: Acyl-CoA oxidase, alcohol oxidase, ascorbate oxidase, bilirubin oxidase, cholesterol oxidase, choline oxidase, glucose oxidase, glycerophosphate oxidase, lactate oxidase, pyruvate oxidase, and sarcosine oxidase are available in bulk from Finnsugar Biochemicals, Inc. (Elk Grove Village, Ill.). In addition, galactose oxidase, glycolate oxidase, oxalate oxidase, L-amino acid oxidase, D-amino acid oxidase, monoamine oxidase, diamine oxidase, cytochrome oxidase, NADH peroxidase, lactoperoxidase, and glutathione peroxidase are available from the Sigma Chemical Company (St. Louis, Mo.). For purposes of this invention, when utilized for electron transferase activity, the oxidase enzymes are referred to as electron transferase enzymes. For instance, Acyl-CoA oxidase is defined as Acyl-CoA electron transferase, alcohol oxidase is defined as alcohol electron transferase, and so on.

It is essential that the enzyme be present in sufficient quantity to react to completion with and remove electrons from the maximum quantity of analyte to be assayed at an acceptable rate, i.e., a rate not too slow nor too fast to be commercially nonviable. Most measurements are completed in a matter of minutes. This particular amount of enzyme will depend upon the particular choice of components and whether an electron transfer agent is being used to promote the transfer of electrons from the enzyme to the other components of the system, thereby regenerating enzyme. Depending upon the requirements of a particular system, the concentration of enzyme can range from about 1.0 to 100.0 IU/ml and higher. Methods for determining the quantity of enzyme to use are known to those skilled in the art.

It is important to note that in accordance with the invention, the electron transferases can be used in conjunction with other protein catalysts (including enzymes) to assay a wide variety of biochemical molecules. The analyte, the concentration of which is sought to be determined, need not be itself a substrate for the electron transferase. It can be, for instance, a chemical or biochemical precursor of the oxidase enzyme substrate. For example, esterified cholesterol can be suitably detected and assayed by use of cholesterol esterase, which produces free cholesterol; the cholesterol is then assayed with a system utilizing cholesterol electron transferase and the other components of the invention as described above. Another example is the assay of triglycerides, which are first reacted with fatty acid lipase to produce a glycerol, which is then assayed by a system using glycerol electron transferase.

The invention can also be utilized in the measurement of the level of a compound that will oxidize a specific other molecule releasing two electrons, for example, the measurement of the levels of an electron transferase enzyme in a fluid, especially a biological fluid. To assay an enzyme, the colorimetric assay system comprises the typical electron acceptor, chromogen and electron transfer agent components. However, instead of comprising an electron transferase enzyme, the system comprises the specific substrate for the electron transferase enzyme to be assayed. The system of the invention is contacted with the enzyme sample for a pre-determined time period. A color change develops indicative of the quantity of substrate consumed by the enzyme, which can be read directly as concentration of enzyme based upon the known reaction rate of the enzyme and the known quantity of time that the reaction was run.

A timing-independent enzyme assay device can be made by incorporating the above system components on a multilayer dry film inserted in a controlled volume capillary. When the enzyme sample of known or unknown concentration is added to this device, the film is hydrated, initiating the enzyme-chemical reaction. One layer of the film will contain a compound capable of diffusing to the enzyme-substrate reaction layer and stopping the reaction. This compound will be added in a preselected quantity for which is known the length of time required for the compound to diffuse to the reaction layer and stop the reaction. The reaction time, enzyme rate and quantity of substrate consumed being known, the enzyme concentration can be calculated.

The use of this assay system in all such combinations is specifically contemplated by this invention.

The enzyme, in effect, serves as a catalytic reaction site for the transfer of electrons from the analyte to the electron transfer agent, chromogen or electron acceptor, as the case may be. In accordance with the invention, therefore, there may be used any compound which is capable of, in the absence of oxygen, removing two electrons from the analyte and releasing them to one or more compounds capable of accepting one or both electrons. Likewise, the invention contemplates the use of any equivalent compounds which are capable of performing substantially the same function as the enzyme in substantially the same manner to obtain substantially the same result.

The quantity of electrons removed by the enzyme from the analyte, corresponding to or indicative of the concentration of analyte, is then colorimetrically assayed.

2. Detailed Description of the Electron Acceptor

It has been found in accordance with the invention that the color change produced by the reduction of chromogen is markedly the chromogen for electrons from the reduced enzyme. In accordance with the invention, the electron sink is defined as an electron acceptor. With this dual component system (chromogen and electron acceptor), it was hoped that the amount of color produced at any given concentration would be retarded and would be at a ratio of less than one molecule of dye per molecule of analyte.

In accordance with the invention, any compound which is capable of irreversibly accepting one or more electrons by having a larger reduction potential than the enzyme may serve as an electron acceptor. Electron acceptance by these compounds must be, for theoretical reasons, reversible. However, it is by far preferable that the electron acceptance be functionally irreversible.

As the case may be, the electron acceptor may accept electrons from either the enzyme, the chromogen, or both.

As stated above, the primary requirement for an ideal electron acceptor is that the electron acceptor have a significantly greater reduction potential than the enzyme. This may be determined experimentally, for example, by spectrophotometric measurement of the amount of electron acceptor reduced in an experimental system containing analyte, enzyme and electron acceptor. The relative reduction potential can be readily calculated by those skilled in the art from the measured equilibrium constant and converted to an absolute reduction potential by comparison to published values for one of the constituents, which can be obtained by reference to Electronegativity Tables published in Mahler and Cordes, *Biological Chemistry*, infra., and Hampel, *Encyclopedia of Electrochemistry* (Reinhold publishing Corp., New York 1964). In choosing an electron acceptor for the reaction having reduced electron acceptor as product, the measured equilibrium constant should be preferably greater than 10 and ideally greater than 20.

Other requirements for the electron acceptor are that neither the native nor the reduced electron-accepting molecule be reactive to inactivate the enzyme used, that the electron acceptor be stable in aqueous solution, and not so reactive that reaction with water occurs (i.e., inert to water) and that the molecule be kinetically capable of accepting electrons at a rate equal to or greater than the rate of the enzyme reaction.

The concentration of the electron acceptor is of critical importance in this invention. In analog to analog measurements, it has been found that the concentration of electron acceptor, and especially the ratio of electron acceptor concentration to chromogen, sets the gain of the a/a control. In analog to digital systems, it has been found that the concentration of the electron acceptor sets the threshold where a sharp color change occurs. Therefore, a wide variety of electron acceptor concentrations can be used, depending upon the concentration of the analyte to be measured, the amount of gain control in an a/a device, or the desired threshold in an a/d device, as will be appreciated by one of average skill-in-the-art.

Depending upon the requirements of a particular system, this concentration may be broadly in the range of about 0.01 to about 500 mM; for practical reasons it may be in the range of about 0.5 to 300 mM; commonly, it is in the range of about 1 to about 200 mM. There are special circumstances where more or less may be suitable. Values of 0.5, 2, 5, 7 up to 150 mM or more are often useful. The optimum concentration depends on the other reactants selected and the preference of the operator. This can readily be determined by one skilled in the art without undue experimentation. Generally, the range of concentrations will be either equal to the analyte concentration range or it will be twice the analyte range if the electron acceptor is a one electron acceptor.

Otherwise, the choice of the electron acceptor is wide. Further, the electron acceptor should be inert with respect to the oxidase enzyme. In addition, when chromogen is present, it is important that the electron acceptor upon accepting an electron, not change color (when it is capable of changing color) in the same visible region as does the chromogen.

Thus, the invention does not exclude e/a which are capable of changing color providing the color change is not in the same visible range as the chromogen.

A particularly effective class of electron acceptors for use in analog to digital systems are ferric chelates, which are defined to include ferric compounds such as ferric EDTA, ferric citrate, ferric oxalate, ferric acetyl acetonate or ferric bipyridyl. For purposes of this invention ferric chelates are defined to include ferricyanide, nitroferricyanide and pentacyanoamino ferrate (III).

A particularly preferred electron-accepting molecule is ferricyanide, which will accept one electron per molecule. Many benzoquinones are useful as two electron accepting molecules, particularly TFBQ and CCBQ, which are useful in analog to analog systems. Another electron acceptor useful in analog to analog systems is TAR. An a/d system may be converted to an a/a system simply by substituting TFBQ, CCBQ or TAR for the a/d electron acceptor. Other useful electron-accepting agents are compounds such as dinitrophenol, metal ions, and molecules with extended, electropositive pi systems, for example 7,7,8,8-tetracyanoquinodimethane.

One useful electron acceptor is the hybrid electron acceptor/electron transfer agent PT radical cation ($PT^{\div}$). $PT^+$ is typically prepared by blending PT, with an oxidizing agent such as ferricyanide, $K_2IrCl_6$, or $NaIO_4$ or by the electrolytic oxidation of PT. However, upon depletion of $PT_+$ there will be no electron transfer agent remaining to promote the transfer of electrons to the chromogen unless a different electron transfer agent is used for the chromogen or a chromogen is used capable of efficiently and directly removing electrons from the enzyme.

What is noteworthy about this compound is that PT will not function as an electron transfer agent unless converted to the radical cation hybrid electron transfer agent/electron acceptor.

In general, one skilled in the art can readily identify additional substances which are suitable electron acceptors, with the assistance of the teaching of the parameters or tests for such compounds as disclosed herein.

In accordance with the invention, compounds which are equivalent in that they are capable of performing substantially the same function as the electron acceptor in substantially the same manner to obtain substantially the same result, are intended to be incorporated herein.

3. Detailed Description of the Chromogen

Suitable chromogens for use in this invention are abundant. Any compound capable of changing color upon reduction by one or more electrons may serve to colorimetrically indicate the analyte concentration. As the case may be, the chromogen may accept electrons from the enzyme, or other electron carrying compounds of lower reduction potential, or both.

The choice of the chromogen is wide and anyone with average skill-in-the-art can select a suitable chromogen for use in this invention. An especially useful chromogen class that has been successfully used are the tetrazolium salts, for example, MTT. These salts have the advantageous feature of being faint yellow in the oxidized form, but turn bright visible colors upon two electron reduction and conversion to formazan dyes. These salts are also capable of removing electrons directly from the enzyme. This advantageously reduces the number of components in a given system by eliminating the need for an electron transfer agent.

Typical of the tetrazolium salts are 2-(2,triazolyl)-3,5-diphenyl tetrazolium bromide (MTT), 3,3'-dimethoxy-4,4'-diphenylene)bis[2-(p-nitrophenyl)-5-phenyltetrazolium chloride](NBT), 2-(p-nitrophenyl)-3-(p-iodophenyl)-5-phenyltetrazolium chloride (INT) or tetranitrobluetetrazolium chloride (TNBT). The concentration of the tetrazolium salt is rather limited by the solubilities of tetrazolium salts and the ultimately formed formazan and generally is less than about 10 mM, with the lower limit set by the amount of reduced chromogen necessary to give a clear and distinct color signal, generally greater than about 0.05 mM.

It is preferable that the reduced form of the chromogen used have a high extinction coefficient, which will result in an intense distinctive color being produced upon reduction of relatively few chromogen molecules. The millimolar extinction coefficient for reduced chromogen is preferably of an order in excess of 10 and ideally in an order in excess of 20. This permits the use of lower concentrations of chromogen, which is preferable in a/d systems. Higher concentrations of chromogen tend to broaden the threshold color change and lower concentrations instead sharpen the color change. The listed chromogens produce dyes that have high extinction coefficients, and the presence of essentially a trace amount of reduced chromogen will generate a color change, for practical purposes, approximately 0.1 mM. Again, it should be noted that the invention is not limited to particular absolute values, and optimum values can readily be determined. Chromogens producing high extinction coefficient dyes are preferred in order to obtain a rapid, sharp and distinct color change in a/d systems.

Other useful tetrazolium salts are disclosed in U.S. Pat. Nos. 4,490,465; 4,491,631; 4,598,042; 4,351,899; 4,271,265; 4,247,633; 4,223,090; 4,215,917; 4,142,938; 4,024,021; 3,867,259; 3,867,257; 3,791,931; and 4,254,222.

Other chromogens capable of removing electrons directly from an enzyme are toluidine blue, methylene violet, methylene green, methylene blue, azure B, janus green B, cresyl blue and methyl eosin. Whether or not a chromogen is capable of directly interacting with the enzyme will, of course, vary with the choice of the enzyme. Glucose electron transferase seems to be a particularly tolerant enzyme in that all chromogens tested have been found to be suitable substrates for this enzyme. However, in general the rate at which chromogen accepts electrons from the enzyme is not optimal and can preferably be improved by addition of electron transfer agent. Some tetrazolium salts, for example, NBT and tetranitro blue tetrazolium (TNBT) are not substrates for cholesterol electron transferase, and require the presence of transfer agent to be used.

In accordance with the invention, compounds which are equivalent in that they are capable of substantially performing the same function as the chromogen in substantially the same manner to obtain substantially the same result, are intended to be incorporated herein.

4. Detailed Description of the Electron Transfer Agent(s)

In accordance with the invention, it has been discovered that the certain compounds defined as electron transfer agents can be used to increase the rate of transfer of electrons from the analyte t the chromogen and electron acceptor.

Because the reaction carried out by the enzyme in this invention is non-physiological, the enzymes have not been optimized for this reaction. Because enzymes are expensive components of any test, they will advantageously be used in as sparingly a manner as possible. The presence of an electron transfer molecule can serve to increase the effective rate of transfer of electrons from the enzyme to the electron acceptor and/or the chromogen, thereby decreasing the amount of expensive enzyme required for any given reaction rate. When presented in this manner, it becomes clear that the electron transfer agent is another catalyst that can serve to increase the rate of transfer of electrons from the source (the analyte) to the ultimate destination, the chromogen or the electron acceptor.

There are a number of reasons why an electron acceptor or a chromogen may be incapable of interaction with a reduced enzyme. It may be that there are no productive binding complexes between the compound and the reduced enzyme. It may be that it is necessary for the enzyme to change conformation into an active form upon binding the compound molecule, which does not occur for the compound in question. Should these or any other equivalent situations apply, an electron transfer agent is used.

Thus, in a general manner, when the e/a or the chr are substantially inert with respect to the reduced enzyme, an e/t/a is commonly used. An e/t/a is also used when the rate of transfer of electrons from the reduced enzyme to either the ea or the chromogen can be advantageously increased by addition of an e/t/a. In this latter case, the e/t/a can be seen as a catalyst that acts to increase the turn-over of the enzyme, reducing the amount of expensive enzyme that needs to be included to obtain any given, desired rate.

Many compounds have been used as electron transferring agents that will accept electrons from the reduced enzyme. One class of compounds generally useful as electron transferring agents are the benzoquinones, particularly 1,4-benzoquinone and 1,4-benzoquinones substituted with electron withdrawing groups such as $-N(CH_3)_3^+$, $-NO_2$, $-CN$, $-SO_3H$, $-COOH$, $-CHO$, $-COR$, wherein R is an alkyl group up to four carbons in length, $-R$, wherein R is as described above, and $-X$, wherein $-X$ is a halogen. Other electron-withdrawing groups are known to those skilled in the art. Typical substituted 1,4-benzoquinones include TFBQ, 2-methoxy-5-methyl-1,4-benzoquinone (MMBQ), 2-cyclohexyl-5-hydroxy-1,4-benzoquinone (CHBQ), 2,5-dichloro-3,6-dihydroxy-1,4-benzoquinone (CPDHBQ), 2,6-ditertbutyl-1,4-benzoquinone (DBBQ), 2,5-dihydroxy 1,4-benzoquinone (DHBQ), 2,6-dimethyl, 4-benzoquinone (DMBQ), 2,5-diphenyl-1,4-benzoquinone (DPBQ), 2,3,5,6-tetramethyl-1,4-benzoquinone (DQ), 2,5-bis (4-fluoroanilino)-3,6-dichloro-1,4-benzoquinone (FADBQ), 2 hydroxy-5-methyl-1,4-benzoquinone (HMBQ), 2-hydroxymethyl-6-methoxy-1,4-benzoquinone (HMMBQ), 2-isopropyl-5-methyl-1,4-benzoquinone (IMBQ), methyl-1,4-benzoquinone (MBQ), phenyl-1,4-benzoquinone (PBQ), tetrachloro-1,4-benzoquinone (TCBQ), DMMBQ, and CCBQ.

Other useful quinones include 4,4-dimethoxy-2,5-cyclohexidien-1-one (DCHDO), 2-hydroxy-1,4-napthoquinone (HNQ), 5-hydroxy-1,4-napthoquinone (JUG), 2-methyl-1,4-napthoquinone (MNQ), rhodizonic acid (RLA), quinhydrone (QH), tetrabromo-1,2-benzoquinone (TBBQ), tetrachloro-1,2-benzoquinone (TCBQ), and tetrahydroxyquinone hydrate (THQH).

Other classes of useful electron transfer agents include flavins such as riboflavin (RBF), alloxazine (ALL) and lumichrome (LC); Phenazines such as phenazine, phenazine ethosulfate, safranine, and PMS; phenothiazines such as PT and its radical cation, PT+, thionin (TH), azure A (AA), azure B (AB), azure C (AC). methylene blue (MB), methylene green (MG) and toluidine blue 0 (TOL); Phenoxazines such as phenoxazine (POA), basic blue 3 (BB3), and brilliant cresyl blue ALD (BCBA); Indophenols such as 2,6-dichlorophenol indophenol (DCIP); and Indamines such as Bindschedler's green and phenylene blue.

It should be noted that there is some enzyme specificity in the choice of electron transferring agents. An agent that has been chosen for one suitable enzyme, may or may not work with another suitable enzyme. This discrimination is not surprising, and in fact is due to the difference in the nature of the pocket on the enzyme that the transfer agent has to penetrate in order to accept electrons. This difference may reflect differences in the hydrophobic nature of the pocket, or of the amount and type of charge surrounding the pocket, or steric constraints. However, the particular e/t/a best suited for the reduced enzyme can readily be ascertained by one of average skill-in-the-art without undue experimentation.

When an electron transfer agent is utilized, the choice of electron acceptor is greatly increased. The requirement for an electron acceptor, other than those listed above, is that the electron acceptor be capable of accepting electrons from the reduced transfer agent. Several inorganic molecules not normally used in biological systems, for example, sodium meta periodate ($NaIO_4$) and $K_2IrCl_6$ can be used.

When an electron transfer agent is included in the system to transfer electrons from the reduced enzyme to the electron acceptor, it is not a requirement of this invention that the reduction potential of the enzyme bear any special relationship to that of the transfer agent. Examples are known (cholesterol electron transferase with DMMBQ transfer agent) where the reduction potential of the transfer agent is smaller than that of the enzyme, so that transfer of electrons from the enzyme to the transfer agent is an energetically up-hill reaction, while other examples (cholesterol electron transferase with TFBQ as transfer agent) are known where the transfer is down-hill. Ideally, the reduction potential of the transfer agent, under the reaction conditions chosen, will not be appreciably less than that of the enzyme, but will be less than that of the electron acceptor so that the equilibrium for transfer of electrons from the transfer agent to the acceptor favors transfer to the acceptor.

The kinetics of transfer of electrons from the enzyme to the transfer agent are not solely determined by the reduction potential of the enzyme and the transfer agent. Indeed, every transfer agent so far investigated shows saturation kinetics with regard to the enzyme. This suggests that a binding site exists on the enzyme for transfer agent, although this invention does not require that such a binding site exist. As is well known in the art, the rate of any reaction that shows saturation kinetics is complex and dependent upon the concentration of the transfer agent relative to its $K_m$ from the transfer reaction, being of first order in transfer agent at concentrations below the $K_m$ and changing to zero order in transfer agent at concentration substantially greater than the $K_m$.

It is surprising that this saturation kinetics is seen. These electron acceptor molecules are not physiological substrates for these enzymes, so that there is no special reason for a transfer agent binding site. Experimental data has demonstrated that one candidate enzyme, cholesterol electron transferase, has at least two binding sites that can be utilized by different transfer agents. One site on cholesterol electron transferase is inhibited by detergent deoxycholate (DOC), while another site is not inhibited. It is known that binding of oxygen to this enzyme is not inhibited by DOC, so that transfer agents that are DOC-inhibited must bind at some site other than the physiological oxygen site. It is not known to which of any sites transfer agents that are not DOC inhibited bind. Further, the invention is not dependent on such underlying possible theories.

One skilled in the art can readily determine which electron transfer agents will work best for a particular enzyme in question. Illustrative enzymes, and their respective suitable transfer agents, are listed in Table 1. For those enzymes not listed, one skilled in the art would test the suitability of candidate electron transfer agent molecules according to the procedure disclosed below.

The analyte is incubated in a solution that contains approximately 2.5 mM ferricyanide, 0.1 to 5 mM candidate transfer agent, enzyme, and a suitable buffer with a pH generally between 6 and 10. The ferricyanide absorbancy at 400 nm is measured. Any decrease in this absorbancy indicates that the transfer agent successfully transferred electrons from the enzyme to the ferricyanide. A control is needed in this test to determine that the ferricyanide does not accept electrons directly from the reduced enzyme at an appreciable rate. A control reaction which contains no enzyme will correct for those candidate transfer agents that changed color during incubation due to a non-specific chemical reaction.

TABLE 1

| ELECTRON TRANSFER AGENTS FOR VARYING ENZYMES | |
|---|---|
| ENZYME | AGENT |
| CHOLINE ELECTRON TRANSFERASE (Choline Oxidase) | TOL, TH, TFBQ, QH, PTHF, MTV, MG, MB, GC, DCIP, AB |
| ALCOHOL ELECTRON TRANSFERASE (Alcohol Oxidase [Candida]) | TFBQ, RRF, QH, PTHF, MTV, MG, AB, DCIP, JGB, DMMBQ, MB, PMS, PT |
| CHOLESTEROL ELECTRON TRANSFERASE (Cholesterol Oxidase [Nocardia]) | PTHF, QH, RRF, TH, TOL, FMN, GC, MB, MTV, AB, CB, MB |
| CHOLESTEROL ELECTRON TRANSFERASE (Cholesterol Oxidase [Streptomyces]) | TH, TOL, DMMBQ, PMS, CV, MG, JGB, PT, AB, BB3, RES, BCBA, ALL, BV, MV, CCCPH, MNQ, RBF, MMBQ, TFBQ, POA |
| GLUCOSE ELECTRON TRANSFERASE (Glucose Oxidase) | PTHF, QH, RES, TH, TOL, DCIP, GC, JGB, MAN, MB, MG, MTV, AB, CB, DMMBQ, HNQ, CCCPH, BV, RHU, MNQ, LC, MV, PMS |
| BILIRUBIN ELECTRON TRANSFERASE (Bilirubin Oxidase) | JGB, QH, POA, ALL |
| LACTATE ELECTRON TRANSFERASE (Lactate Oxidase) | TOL, FMN, POA, BV |
| PYRUVATE ELECTRON TRANSFERASE (Pyruvate Oxidase) | AB, QH, TH, MAN, DMMBQ |
| XANTHINE ELECTRON TRANSFERASE (Xanthine Oxidase | FMN, POA, PT, RES |
| MONOAMINE ELECTRON TRANSFERASE (Monamine Oxidase) | DCIP, RES, PT, PMS |

TABLE 1-continued

ELECTRON TRANSFER AGENTS FOR VARYING ENZYMES
ENZYME    AGENT

BV = Benzyl Viologen
CCCPH = Carbonylcyanide-3-chlorophenol hydrazone
CV = Cresyl Violet acetate
FMN = Flavin Mononucleotide
GC = Gallocyanine
HNQ = 2-Hydroxy-1,4-napthoquinone
JGB = Janus green B
MAN = Bis-N-Methyl-acridinium nitrate
MNQ = 1-Methyl-1,4-naphthoquinone
MTV = Methylene violet
MV = Methyl viologen
PTHF = 9-Phenyl-2,3,7,-trihydroxy-6-fluorone
QH = Quinhydrone
RES = Resazurin
RHU = Ruthenocene
RRF = Resorufin The reduction potential relationship necessary between the electron transfer agent and other system components and the means by which this value relative to the other components may be determined was discussed above. Generally any molecule capable of interacting with an enzyme to remove one or more electrons and then transferring said electron(s) to either a chromogen, electron acceptor, or both can be used in this system.

It is advantageous that the electron transfer agent transfers electrons to both the electron acceptor and the chromogen. This promotes the local equilibrium preferable for an efficient a/d device by preventing the build-up of electrons on the chromogen while non-reduced electron acceptor is available.

It is noteworthy that a particular advantage to this system is that electron transfer agent molecules capable of interaction with enzymes for removal of one or more electrons are regenerated upon transfer of electrons by electron-carrying electron transfer agents to chromogens or electron acceptors. For this reason, large amounts of electron transfer agent are not needed. A quantity is used sufficient to transfer electrons at an acceptable rate, generally a trace amount, that, for practical purposes, is approximately 1 mM.

It should be noted that many chromogens are capable of acting as electron transfer agents themselves, though perhaps more slowly and less effectively than does the added electron transfer agent. A kinetically more rapid pathway must exist for transfer of electrons from any reduced chromogen (dye) that may exist to the electron acceptor.

It is especially important when assaying a multi-phase system that a kinetically rapid pathway be provided for the transfer of electrons to the electron acceptor from any reduced chromogen that may have accumulated. The term "multi-phase" is intended to include "dispersions". One example of a multi-phase system is a system containing aqueous and non-aqueous phases. Typical of such a system would be the assay of a lipid-soluble analyte such as cholesterol, fatty acids or triglycerides suspended in an aqueous phase, or the assay of a water-soluble analyte such as glucose in a lipid containing fluid, such as blood serum. However, all phases of a multi-phase system can be aqueous, such as polymer-salt aqueous two-phase systems well known in the art. It is not necessary for the solution to exhibit two or more distinct phases in order to qualify as multi-phasic. For example, all detergent solutions and all solution-containing suspended lipids (e.g., serum), act as multi-phase solutions.

When an aqueous/non-aqueous two-phase system is assayed, for example, the components of the colorimetric assay system of the present invention will tend to partition between the aqueous and non-aqueous phases based upon their relative hydrophobicity. For example, when the chromogen is MTT and the electron acceptor is ferricyanide, the formazan formed from the chromogen is more lipid-soluble than the electron acceptor and each component tends to migrate to separate aqueous and non-aqueous phases. The electron acceptor isolated in the aqueous phase fails to encounter electrons in the non-aqueous phase, which instead reduce the chromogen isolated in the lipid phase.

To get the sharp color-change break important for the accurate functioning of the system, the system must be at local equilibrium at all times. Kinetically determined meta-stable states that give rise to false readings cannot exist.

It is therefore advantageous to add to the system an electron transfer agent that catalyzes the transfer of electrons to the electron acceptor from accumulated reduced chromogen. Without this additional electron transfer agent, the phase transfer rates of the electron acceptor o the chromogen determine the reaction rate of the system. This electron transfer agent may be the same compound as the one that removes electrons from the enzyme. Ideally, this agent for the transfer of electrons from the chromogen to the electron acceptor is a molecule which is present in a catalytic amount with a reduction potential midway between that of the electron acceptor and chromogen and freely soluble in both the aqueous and lipid phases. Accordingly, this may not be the same electron transfer agent that accepts electrons from the enzyme for transfer to the electron acceptor and/or chromogen.

A simple test can determine all of the above ideal criteria. Reduced chromogen is made chemically (for example by reduction with a molar equivalent of bisulfite), then scanned in the visible region to determine the wavelength of maximum absorbancy and the extinction coefficient. A known amount of electron acceptor and an optional amount of transfer agent are added, and the rate and amount of reduction of color is determined. The amount of color reduction can be used to directly calculate the equilibrium constant (the difference in reduction potential) for transfer of electron from the reduced chromogen to the electron acceptor, while the rate of this transfer can determine if a pathway exists that is rapid compared to the rate of the enzymatic reaction.

In accordance with the invention, therefore, the invention comprises systems with a multiplicity of electron transfer agents. Typical of such a system would be one in which PT radical cation is used as the electron acceptor, DMMBQ is used as the electron transfer agent, NBT is used as the chromogen, and TFBQ is used as the agent for transferring electrons to the electron acceptor from accumulated reduced chromogen.

It should be noted that use of an additional electron transfer agent to provide a kinetically fast pathway between the chromogen and electron acceptor is not limited to multi-phase systems. In any system, the chromogen can acquire electrons through random collisions with the electron transfer agent, even in analog to digital systems in which the electron transfer agent ordinarily transfers electrons preferentially to the electron acceptor over the chromogen. The additional electron transfer agent provides a kinetic pathway by which these electrons may be transferred to the electron acceptor from such accumulated reduced chromogen. Accordingly, the use of a second electron transfer agent in analog to digital systems is preferred when fine measurement is required.

In accordance with the invention, compounds which are capable of substantially performing the above-defined function of the electron transfer agent in substantially the same manner to obtain substantially the same result are intended to be incorporated herein.

Although the choice of the electron acceptor, chromogen, and electron transfer agents will vary with each individual system, and some systems will function without separate electron transfer agents or chromogens, the criteria for ideal components for the invention is described hereinafter.

The ideal electron transfer agent will be that which is capable of transferring electrons from the enzyme at the maximal rate, and will have a reduction potential between that of the enzyme and the chromogen or electron acceptor. When this case is met, there is no energy barrier for transfer of electrons from the enzyme to the transfer agent, and the transfer of electrons from the transfer agent to the electron acceptor or chromogen will likewise be energy-wise favorable so that at steady state, reduced transfer agent does not accumulate and the transfer agent active form (non-reduced) is present in concentrations approaching the total concentration. It is also advantageous that the transfer molecule efficiently catalyze electron transfer between the reduced chromogen and the electron acceptor (and vice-versa) so that kinetic considerations do not prevent the system from being in local equilibrium during the course of the reaction.

5. Further Detailed Description of Analog to Analog and Analog to Digital Systems There are in accordance with the invention, two sub-embodiments, an analog to analog system, wherein the affinity of the electrons for the electron acceptor and chromogen is approximately within the same range of magnitude; and an analog to digital system wherein the electrons have a greater affinity for the electron acceptor than for the chromogen.

In the analog to analog sub-embodiment, the color generated by the chromogen is at a non-zero initial rate. The relative mole percent of chromogen to electron acceptor, useable in accordance with the invention, varies over a wide range. One skilled in the art can determine readily the optimum relative proportions of the two compounds, which would vary depending on the intensity of the colored dye generated by the chromogen. If the chromogenic substrate is such that it would not generate a very large excess of dye beyond that which can be readily colorimetrically measured, the proportion of electron acceptor that needs to be present is in a smaller proportion than if the chromogen is such as to generate a larger or more intense excess of color determinable colorimetrically. Likewise the relative proportions will depend on the nature of the analyte and the amount of the analyte in solution which is sought to be determined.

In general, the proportion of electron acceptor is at least as much as will cause a decrease in the amount of reduced chromogen generated by the oxidation of analyte. The maximum of electron acceptor should not be such as to cause the amount of colored dye generated to be so small as not to be measurable colorimetrically. In general, the relative molar proportion of electron acceptor to chromogen ideally should be at a ratio equal to or greater than 1 to 1 but the proportion either way may vary and be in excess of the other under certain circumstances, ranging to a ratio greater than about 400 to about 1 with respect to the other, and depending on the amount of color reduction required. In general, though, an excess of chromogen over electron acceptor is not desirable for this could generate additional colored dye after the electron acceptor is exhausted. The reverse condition will advantageously extend the colorimetrical range of color response.

Of course what has been described above applies likewise for the aspect of the invention where rather than developing a colorimetrically measurable color the amount of color is decreased from an intense color to a color within a colorimetrically determinable range.

In order that partition of electrons does not favor the electron acceptor over the chromogen, or vice-versa, the reduction potential of the chromogen should be similar to that of the electron acceptor. The preferred chromogen will have a lower extinction coefficient in order that the electrons need not be partitioned predominantly to the electron acceptor over the chromogen to maintain a linear relationship between the degree of color change and analyte concentration.

In accordance with the analog to analog system of the invention, the degree of color change generated plotted against analyte concentration gives a straight and reproducible line. Thus, the concentration of an unknown amount of analyte is determined by comparison of color formed by the unknown sample and a linear standard curve produced by known samples.

In the analog to digital sub-embodiment, the electron acceptor is preferentially irreversibly reduced prior to chromogen reduction. However, the relative molar proportions of these two components are in the same proportions as in the above-discussed analog to analog systems. It should be noted, however, that in the analog to digital system, no color will be generated unless there is sufficient quantity of the analyte present to allow for the complete reduction of the electron acceptor, after which reduction of the chromogen and a color change will proceed.

In this sub-embodiment, when the amount of color generated by the chromogen is plotted against the analyte concentration, there is shown a generated linear relationship after a delay which corresponds to the time or amount necessary for the electron acceptor to be reduced, during which delay no visible color is generated. During that period, essentially no chromogen is reduced, at least not enough to generate a visible color change. In this sub-embodiment of the invention, the affinity for electrons of the e/a should be greater than that of the chr and/or e/t/a, so that no reduction of the chromogen takes place until all, or virtually all, of the electron acceptor is exhausted. Under certain circumstances, the color development will start even though there may still be an amount of about 2 mM of electron acceptor present.

In order that the affinity of the e/a be greater for electrons than that of the chromogen, the reduction potential difference between the chromogen and the electron acceptor should be maximized. In addition to this reduction potential criterion, the ideal chromogen will have a large extinction coefficient upon reduction in order to sharpen the color transition at the threshold.

If electrons are not transferred preferentially to the electron acceptor over the chromogen, but are shared between them, then the system is an analog to analog system and not an analog to digital system.

It is well known in the art that the reduction potential of pairs of molecules can be directly related to the equilibrium constant for a reaction. As the chromogen has a reduction potential less than the electron acceptor, the equilibrium constant for transfer of electrons from the reduced chromogen to the electron acceptor, either directly or mediated by added electron transfer agent, will be greater than one. When the equilibrium constant is greater than 10, the system will be an a/d system. When the equilibrium constant is less than 10, the system will be either a/a or a/d, depending upon the nature of the chromogen. Regardless of the reduction potential relationship between chromogen and electron acceptor, the equilibrium constant for the transfer of electrons to either from the reduced enzyme should remain, as discussed above, at least 10, and preferably greater than 20.

In accordance with the invention, unlike the analog to analog sub-embodiment, no color will be generated unless a pre-determined amount—the threshold amount—of the analyte this situation color is only generated when analyte is present in an excess over the amount necessary for the reduction of the electron acceptor. This amount is pre-determined by determining at what minimum concentration a color will be developed from the analyte selected. Thus, this system allows a digital "on-off" reading which determines whether analyte is present in a concentration greater than the pre-determined threshold. The system for determination of the amount of analyte to be tested contains varying concentrations of electron acceptor up to and in an amount in excess of the minimum amount.

It is preferred, in an analog to digital system, that the sharpness of the threshold color break be maximized. There are several considerations to maximizing the sharpness of this transition point, from colorless to colored. The greater the reduction potential difference between the electron acceptor and the chromogen, the sharper will be the transition at the threshold. Thus, in cases where very fine measurement is required, the chromogen/electron acceptor pair should be chosen to maximize this difference. In addition, the visible color change that the chromogen undergoes upon conversion to the dye should be as great as possible. This difference is measured as the extinction coefficient difference of the chromogen/dye pair, as is well understood by those with average skill-in-the-art.

In accordance with the invention, the reaction may be carried out in a liquid or on a suitable physical carrier which allows for the reactants to react as described. Suitable physical carriers and devices embodying these carriers are disclosed in U.S. Pat. No. 4,059,407 which is incorporated herein by reference and in copending application Ser. Nos. 942,414 filed Dec. 16, 1986; 075,817 filed Jul. 20, 1987; and 106,745 filed Oct. 9, 1987, all of which are incorporated herein by reference. The disclosure of suitable physical carriers and devices embodying these carriers disclosed in the specification of co-pending application Ser. No. 106,745 from page 24, line 5 to page 27, line 6, and from page 41, line 14 to page 42, line 6, is specifically incorporated herein by reference.

The invention is not limited to the particular physical embodiments described above. There are numerous appropriate physical arrangements that are described in the literature and others can be built by one of average skill-in-the-art.

Prior art provides descriptions of devices, often disposable, which may be used in the practice of this invention as such or in a modification of such devices. Reference for such devices is made to U.S. Pat. No. 4,059,407; and the patents listed therein; 3,464,871; 3,992,158. These patents describe a multilayer analytical element that will change color in the presence of an analyzed molecule, such as a multilayer dry film or gel situated inside of a controlled-volume support capillary. The capillary need not be oxygen-permeable. The technology discussed in these patents yields a analog color signal for an analog concentration input. Reference is also made to U.S. Pat. Nos. 3,485,587 and 3,164,534.

FIG. 1 shows an embodiment of the invention. The diagnostic device includes:

A sample entry port (1), which can be of variable configuration depending on the nature of the test and the analyte-containing fluid chosen, a membrane separation arrangement (2) for separating insoluble and colloidal solids (for example, red blood cells from blood) from the fluid, a capillary measuring area (3) where the chemical/enzymatic reaction takes place, an air exhaust port (4) allowing the displaced air to escape from the capillary measuring region as the fluid fills this region, for example by capillary action, and a film of one or more layers (5) containing the system ingredients in a dry format; this film contains different concentrations of electron acceptor molecules at different regions of the capillary measuring region.

FIG. 2 and FIG. 3 are side and top views of a similar diagnostic device in which the support member is a Vacutainer® Blood Collection Tube. The method of the invention utilizing this particular device comprises placing one end of a common, double-pointed, blood collection needle in a patient's vein, the other end is then pushed through the rubber stopper (6). The vacuum bulb (7) in the device pulls a venous blood sample into the glass or plastic tube (8) of the device. Drawn by the vacuum, the serum is separated from the red blood cells by a membrane (9). The serum then flows into the capillary measuring area (10) until the area is full and the vacuum in the vacuum bulb is depleted. The dry film (11) in the capillary measuring area then hydrates and the enzymatic reaction takes place.

A device of such construction is read in the same way as a thermometer (FIG. 3).

In the depicted devices when the capillary region is filled with the biological fluid, the system reaction takes place. At those regions in the capillary measuring region where the analyte concentration to be measured is greater than the electron equivalent concentration of electron acceptor molecules, a visible color change will be observed. In those regions where the analyte concentration is less than the electron equivalent concentration of electron acceptor, no color change will be observed. Thus, if the capillary measuring regions contain an increasing linear or step gradient of electron-accepting molecule, the concentration of analyte can be read as the distance of color change along this gradient. This distance of color change can be compared to a grid imprinted onto the device and directly read as analyte concentration.

The embodiments thereby provide a practical measuring device of numerous industrial and commercial applications. Some applications will involve the coupling of the device to a sampling means such as a lancet with which a blood sample is taken for the assay of serum analytes, especially cholesterol or glucose. Other applications will involve the coupling of the device to a data processing or storage means, such as a microprocessor. The data may be hand-entered by one using the invention into the data processing or storage means, or the device read-out may be machine-converted to a processable signal, for example, by way of optical scanning. Such data processing and storage means could be used to determine serum HDL/LDL ratio values from measurements of serum triglycerides and cholesterol, or such a means could be used for diabetics to store the results of successive serum glucose tests to process the data into a short-term history or profile. This would be especially useful information for diabetics to maintain between periodic visits to their doctor.

When, in accordance with the invention, it is desired to measure the concentration of a biochemical analyte, the method comprises bringing together the electron acceptor and, as the case may be, the chromogen and/or the electron transfer agent, together with a specific electron transferase for the organic substrate to be measured. This mixture is brought together with the analyte sample, causing the enzyme to be reduced and the reaction to proceed until a color change is generated, as described herein above. At this point the non-reduced electron acceptor is depleted and the reduced enzyme reacts with chromogen to yield reduced chromogen and a highly visible color change indicative of the concentration of the analyte.

Generally the reaction is carried out in a buffered environment at a pH at which the enzyme is active, and in the presence of the other components used, as is described hereinafter, and at optimum temperatures. Generally, the temperature is ambient or room temperature. The pH is generally in the range of about 4 to about 11 (being optimized for the different enzymes used). The optimum pH ranges for different enzymes, or for the same enzymes of different origins, are known. The temperature can be in a range in which the enzyme is active. Stabilizers (for the enzymes or the resulting dyes) can be used, and if desired, wetting agents. Illustrations are BSA, polyalcohols, mild reducing agents, and non-ionic surface active agents.

In accordance with the system of the invention, the analyte the concentration of which is to be assayed can be virtually any organic compound capable of being a substrate for an electron transferase enzyme system. Generally, any substrate capable of electron transferase activity with an enzyme may be used. As stated above, this includes substrates having activity with the oxidase enzymes listed in Barman, *Enzyme Handbook*, supra. Typical analytes of interest include acyl-CoA, sugars such as glucose, lactose and galactose; polyalcohols such as glycerol and sorbitol; blood serum components such as albumin, triglycerides, cholesterol, bilirubin and hemoglobin; alcohols such as ethanol and methanol; caffeine, urobilinogen, nitrates, nitrites, digoxin, digitoxin, thyroxine, triiodothyronine, creatinine, urea, xanthine, lactate, pyruvate, oxalate, choline, sarcosine, cytochromes, NADH, and glutathione; amine compounds such as mono- and di-substituted amines such as spermidine and amphetamine, L- and D-amino acids, and other proteins; ketones and organic acids like lactic acid, pyruvic acid, oxalic and, ascorbic acid and uric acid; aldehydes like formaldehyde and acetaldehyde; xanthines such as caffeine, theophylline and theobromine; beta-hydroxybutyrate and antibodies and antigens, monoclonal or otherwise, (like hepatitis B surface antigen, antigen(s) of acquired immune deficiency syndrome, immuno deficiency virus, HIV I or HIV II or variants thereof, and others); nucleotide sequences, glycerol-3-phosphate, glycine lactate and various other organic substrates that are reactive to oxygen-free enzyme-catalyzed oxidation and others disclosed in the literature. For example, one skilled in the art could, with the system of the invention, devise methods and devices for the assay of the biochemical molecules disclosed in *Documenta Geigy: Scientific Tables* (6th Ed., Ed: K. Diem, Geigy Chemical Corp., Ardsley, N.Y., 1962).

The fluid in which the analyte is borne is not important to, or a limiting aspect of, this invention. The scope of this invention extends far beyond the specific examples used for the purpose of discussion and illustration in the experimental methods section.

Commonly the substrate is present in a biological fluid like serum, blood, urine, semen, saliva, cerebrospinal fluid or other liquids of humans or other mammals.

The fluids are not limited to those obtained from humans but also include those obtained from other mammals in general, including, for example, bovine, porcine, equine, ovine, feline and canine fluids. The fluids also include those obtained from non-mammals such as fish and birds. The fluids can also be obtained from plants or protists. The organisms can be naturally-occurring or genetically engineered.

Commercial applications for this invention are numerous and include the measurement of environmental pollutants such as aliphatic and aromatic hydrocarbons and chlorinated aliphatic and aromatic hydrocarbons; the measurement of bodily fluid levels of therapeutic drugs such as theophylline, theobromine, cyclosporin and various antibiotics, members of the alkaloid family, both therapeutic and illicit, and the measurement of bodily fluid levels of other controlled dangerous substances such as various amphetamines, opiates and tetrahydrocannabinols (THC's). The assay of other organic molecules and the exploitation of commercial applications, which would be obvious to one of ordinary skill-in-the-art, is specifically contemplated by this invention.

In one method, this invention can also be used with any mixture of enzymes to assay a biological molecule providing one of the resulting products of this mixture or string of enzymes is a reduced electron transferase enzyme. The use of mixtures of enzymes in the assay of biological molecules or of enzymes is known to those skilled in the art. There is a potentially unlimited number of different combination of enzymes that can be combined by one skilled in the art so that a resulting product is a reduced electron transferase enzyme. A list of such enzymes would be obvious to those skilled in the art of enzyme assays.

It is specifically noteworthy that in another method, this invention is also useful in the determination of the activity of any electron transferase enzyme, or combination of enzymes, that result in the reduction of an electron transferase enzyme.

For example, the amount of an electron transferase enzyme is determined by the rate at which color is produced in a system combining the enzyme's specific substrate, necessary buffer salts, the components of the invention and an unknown amount of the enzyme.

It is important to note that in accordance with the invention, the compound, the concentration which is sought to be determined, need not be itself a substrate for the enzyme. It is sufficient that it be capable of generating a substrate for the enzyme. In this manner the analyte the concentration which is sought to be determined produces a reagent substrate from one or more reactions "upstream", which in turn reacts with the electron transferase enzyme in accordance with the invention.

It is to be noted that it is within the scope of the invention to use more than one electron acceptor (inert with respect to each other) which will be sequentially reduced in accordance with the invention. Likewise there may be used more than one chromogen. Similarly, the system can be used to assay more than one organic analyte (with their respective enzyme), which analytes may have different reactivity levels with respect to other reactants.

For example the serum HDL/LDL ratio for cholesterol can be determined by the assay of total cholesterol, HDL cholesterol and triglycerides. Cholesterol consists of three components which may be expressed as the following:

TOTAL CHOLESTEROL = HDL + LDL + VLDL

HDL concentration may be assayed by first precipitating HDL out of a serum sample by reacting the sample with manganous ion. The difference is total cholesterol level before and after HDL precipitation is the HDL concentration.

VLDL concentration is equal to two per cent of triglyceride concentration. For this reason triglyceride concentration is assayed.

Once levels of total cholesterol, HDL and VLDL are determined, the LDL level, and consequently the HDL/LDL ratio, can be calculated.

It is within the scope of the invention also to use the method of the invention on a continuous basis in a device adapted to feed the reactants to a multiplicity of reaction zones for the reactions to take place and the color changes to develop.

Such device is likely to be of particular interest for industrial purposes like monitoring the absence, presence or concentration of organic compounds.

Although the present invention has been described and illustrated in connection with preferred embodiments, it is to be understood that modifications and variations may be made without departing from the spirit of the invention as those skilled in the art will readily understand. Such modifications are considered to be within the purview and scope of the present invention as defined by the appended claims.

The invention having been described adequately to one skilled in the art to make use of it to the extent desired, the following examples are merely illustrative of the invention, and in no way are to be construed as limiting the invention. It is evident that without undue experimentation, one skilled in this art can make many and suitable substitutions or variations and still be within the scope of the invention and obtain substantially the same results without departing from the teaching and spirit of the invention.

All parts are by weight unless indicated otherwise.

The following examples are shown of illustration 1, discussed above.

EXAMPLE 1

An analog to digital colorimetric measurement of cholesterol

Solutions containing 4, 4.5, 5.0, 5.5, 6.0, 6.5 and 7 millimolar (mM) cholesterol are added to separate test tubes containing:
- 50-200 mM buffer at a pH between 8.7 and 9.7
- 11% Triton X-100
- 11.4 mM ferricyanide (electron acceptor)
- 0.5 mM MTT (chromogen)
- 1 mM PMS (electron transfer agent)
- 136 IU/m Cholesterol electron transferase (Streptomyces cholesterol oxidase) (enzyme).

The solutions containing 4, 4.5, 5.0, and 5.5 mM of cholesterol did not show any color change from the original pale yellow cast, while the cholesterol solutions in excess of the 5.7 mM threshold concentration turned deep blue.

EXAMPLE 2

An analog to digital colorimetric measurement of glucose

Example 1 was repeated as above except that Triton X-100 was omitted, glucose was substituted for cholesterol and glucose electron transferase was substituted for cholesterol electron transferase. The pH was lowered to about 5.6. Again no color change was observed when up to 5.7 mM glucose was added to the reaction. A bright blue color was observed when a glucose concentration of at least 5.8 mM and greater than this amount was added.

EXAMPLE 3

Example 2 was repeated, except that 200 IU/ml catalase was added to the test tube. This enzyme rapidly destroys hydrogen peroxide. Identical results to those in Example 2 were obtained.

Example 2 was again repeated, except that the reaction media was made oxygen-free by repeated vacuum nitrogen purge cycles. Oxygen-free glucose solutions were then added under nitrogen. Identical results to those in Example 2 were obtained.

This Example conclusively proves that neither molecular oxygen is a reagent, nor hydrogen peroxide a product, of the reaction mechanism of the present invention, distinguishing the present invention from the above-cited prior art.

Thus as amply described earlier herein the system (amid the reactions involved) is not oxygen-dependent, does not yield H2O2, and yet can take place in the presence of oxygen.

EXAMPLE 4

An analog to digital colorimetric read-out of alcohol concentrations

Ethanol in 1 mM increments from 20 to 30 mM was added to a series of solutions containing:
- 150 mM tris chloride buffer, pH 8.0
- 50 mM $K_2IrCl_6$ (electron acceptor)
- 10 mM PT (electron transfer agent)
- 1 mM INT (chromogen)
- 100 IU/ml alcohol electron transferase (alcohol oxidase) (enzyme) and
- 200 IU/ml catalase.

Those reactions containing alcohol concentrations less than or equal to 25 mM did not change color; all solutions with alcohol concentrations above 25 mM turned bright red.

The chromogens MTT, NBT, TNBT, MV, BV, BB3, AB and MB function interchangeably when either ferricyanide, ferric chelates or $K_2IrCl_6$ is the electron acceptor for analog to digital analyte-enzyme systems. The chromogens MTT, NBT, TNBT, MV and BV function interchangeably when the electron acceptor is $PT^+$ prepared from either $KIO_4$, ferric citrate, ferric oxalate or ferric EDTA, for all analog to digital analyte enzyme systems.

EXAMPLE 5

An analog to analog, oxygen independent, colorimetric measurement of bilirubin Varying concentrations of bilirubin, from 0 to 5 mM, are added to a solution containing:
- 1.7 mM MTT (chromogen)
- 5-150 mM pyrophosphate buffer, pH 7-10
- 5 to 30 mM TFBQ (analog electron acceptor)
- bilirubin electron transferase (bilirubin oxidase (enzyme)
- 0.5 mM PMS (electron transfer agent)

The intensity of the MTT color change produced is linearly proportional to the bilirubin concentration, even at bilirubin concentrations nearly three times that of the chromogen, illustrating that less than one molecule of MTT is reduced for every molecule of bilirubin oxidized.

TAR, 2,5-dihydroxy-1,4-benzoquinone and 2-cyclohexyl-5-hydroxy-1,4 benzoquinone, and N-1-methylflavin are functional analog electron acceptor substitutes for TFBQ in this example, and with all analog to analog analyte-enzyme systems. The chromogens MTT, INT, and TNBT function interchangeably in all analog to analog analyte-enzyme systems of this example not utilizing TFBQ as the analog electron acceptor. The electron transfer agents DMMBQ, PMS and POA also function interchangeably in all analog to analog analyte-enzyme systems of this example, and in systems in which it is not an electron acceptor, TFBQ also functions acceptably as an electron transfer agent.

EXAMPLE 6

An analog to digital device for the "machine independent" determination of serum glucose levels This device consists of a measuring area composed of a defined volume of ceramic material, such as alumina, that is capable of absorbing a set and reproducible amount of fluid, and that is coated with an oxygen impermeable barrier. This device contains a region where serum can be applied to one end of the ceramic measuring area (or blood, if a membrane that will pass serum but not blood is coated over the ceramic end). The ceramic measuring area is, prior to insertion in this device, dipped in a solution of:
- citrate-phosphate buffer, pH 4.5 to 8.5
- glucose electron transferase (glucose oxidase)(enzyme)
- 1 mM MTT (chromogen).

This ceramic measuring area is then dried. A multiport coating head then deposits a linear gradient, from 10 to 100 mM, of:
- PT radical cation hybrid electron acceptor and transfer agent prepared by mixing equal molar amounts of PT and electron acceptor (ferricyanide or $K_2IrCl_6$ or $NaIO_4$ or alternatively, by electrolytic oxidation of PT).

When serum is added to this device, a blue bar develops that is indicative of the concentration of glucose in the serum or blood. In this manner different concentrations of glucose of 10, 25, 45, 50, 80 and 100 mM were measured. The device as outlined has a dynamic range of 10 to 100 mM glucose, far greater than the dynamic ranges currently existing in colorimetric glucose measuring devices.

EXAMPLE 7

An analog to digital colorimetric measurement of serum cholesterol in a multi-phase fluid Samples of blood serum containing both free and esterified cholesterol with a concentration between 150 and 400 mg/dl are prepared by reacting the serum samples with an enzyme or set of enzymes containing cholesterol esterase activity.

Samples are then added to devices composed of multilayer dry film situated inside of 50 microliter controlled-volume, oxygen-impermeable support capillaries. In each capillary, one film layer contains:

- 1% Triton X-100, 0.5% PEG, 50 mM potassium phosphate buffer (KPi), pH 8.0 (buffer)
- 0.8 mM MTT (chromogen)
- 2.0 mM PMS (primary electron transfer agent)
- 1.0 mM POA (secondary electron transfer agent)
- 150 IU/ml cholesterol electron transferase (cholesterol oxidase from a microbial source) (enzyme)

The other layer contains a linear gradient of ferric EDTA from 2.0 mM at the end of the capillary measuring area nearest to the serum entrance to 14 mM at the opposite end.

When the serum samples of known or unknown cholesterol concentration are added to the devices, the serum is drawn into the capillary, whereupon it hydrates the dried film and initiates the enzymatic chemical reaction. The detergent emulsifies the cholesterol forming ionic and micellar aqueous phases with the ferric EDTA and MTT partitioning between the ionic and micellar phases, respectively. Any premature accumulation of chromogen reduced by reduced enzyme in the micellar phase is eliminated by POA, which removes electrons from the reduced chromogen, preferentially located in one layer, diffuses to the electron acceptor in the other layer, and transfers the electrons to the ferric EDTA.

As the reaction rapidly progresses, a blue bar develops that is indicative of the concentration of cholesterol in the serum or blood. In this manner different concentrations of cholesterol of 175, 215, 265, 275, 350 and 400 mg/dl were measured.

For the assay of glucose in serum, the secondary electron transfer agent is deleted, glucose electron transferase (glucose oxidase) is substituted for cholesterol electron transferase, and 25 mM KPi buffer, pH 7.4 is substituted for the buffer, eliminating the detergent.

EXAMPLE 8

An analog to digital colorimetric measurement of serum triglycerides in a multi-phase fluid The devices of Example 7 were repeated as above, except that 40 IU/ml glycerol electron transferase (glycerol oxidase), 80 IU/ml lipase, and 5% Brij 35 to solubilize serum triglycerides was substituted for cholesterol electron transferase, CCBQ was substituted for POA as the secondary electron transfer agent, and the initial treatment of the serum sample with cholesterol esterase was omitted.

When the serum samples of known or unknown triglyceride concentration are added to the devices, the dried films hydrate and initiate the enzymatic chemical reactions that convert the triglycerides to glycerol, which is assayed by glycerol electron transferase. The detergent emulsifies the triglyceride, forming the ionic and micellar aqueous phases into which the ferric EDTA and MTT partition. Premature accumulations of reduced MTT are eliminated by CCBQ, which transfers electrons from the reduced MTT to ferric EDTA.

As the reaction rapidly progresses, a blue bar develops that is indicative of the concentration of triglycerides in the serum or blood. In this manner different concentrations of triglyceride of 40, 110, 250, 460, 740 and 10% mg/dl were measured. The devices have a dynamic range of 0 to 4000 mg/dl triglycerides.

EXAMPLE 9

Determination of the HDL/LDL serum cholesterol ratio

Examples 7 and 8 were repeated on serum samples from a fasting patient to obtain concentration levels for total cholesterol and triglycerides. HDL cholesterol was precipitated from a third sample by reacting it with 50 mM $MnCl_2$. Example 7 is then repeated on the supernatant serum to obtain a concentration level for the total cholesterol with HDL removed. The difference in the two values is the HDL concentration.

The LDL concentration is obtained by subtracting the values for HDL concentration and VLDL concentration from total cholesterol. VLDL concentration is obtained by dividing the triglyceride concentration by 50.

The final value is expressed as a ratio of HDL to LDL.

EXAMPLE 10

An analog to digital device for the machine independent determination of cholesterol concentrations A device such as pictured in FIG. 1 contains: a means for producing a blood sample into a vacuum containing tube (1), a membrane filter (2) for separating blood cells from serum, permitting passage of serum into a capillary measuring area (3) containing a multilayer dry film (5), one layer of which contains a linear gradient of ferricyanide or ferric oxalate (electron acceptors) from 0 mM at the end of the capillary measuring area nearest to the serum entrance to 25 mM at the opposite end. The other layer contains:

- 80 mM borate buffer, pH 8.0 to 9.7
- 0.25 mM Azure B (Chromogen)
- 12 mM MMBQ (electron transfer agent)
- 28 IU/ml cholesterol electron transferase (cholesterol oxidase) (from Streptomyces or Nocardia) (enzyme)
- 75 IU/ml cholesterol esterase and
- 5% Brij 35 to solubilize serum cholesterol When blood of known or unknown cholesterol concentrations is added to this device, the vacuum in the device causes the serum to flow through the membrane and separate from the red blood cells. The vacuum then draws the serum into the capillary, whereupon it hydrates the dried film and initiates the enzymatic/chemical reaction. Azure B, upon reduction changes from colored to colorless. The device is made of a colored bar which, when serum is added turns colorless, (or bleached), along the linear gradient, to an extent linearly related to the cholesterol concentration of the sample. In effect, the colored bar becomes shorter to a degree directly dependent upon increasing cholesterol concentration.

In this example, DMMBQ or CCBQ are also quite acceptable electron transfer agents that function without loss of either cholesterol concentration discrimination or assay speed.

MTT, NBT, or TNBT are acceptable chromogens in place of Azure B. These chromogens are desirable because they effect a color change from colorless to colored instead of bleaching at those concentrations of cholesterol greater than the threshold. Thus a colored bar of various length, linearly related to increasing cholesterol concentration is produced. The pH range of this device can be significantly altered solely by changing the source of enzyme. For example, substitution of Schizophyllum cholesterol electron transferase can be used in place of any of the above enzymes at a pH range from about 3 to about 7.

When glucose electron transferase (glucose oxidase) is substituted for cholesterol electron transferase and esterase, the colorimetric device functions to assay serum glucose.

EXAMPLE 11

An analog to digital measurement of lactic acid in cerebrospinal fluid

Samples of cerebrospinal fluid are introduced into 50 microliter controlled volume capillaries each having a dried film containing approximately:
 0.8 IU lactate electron transferase (lactate oxidase) (enzyme)
 0.5 mM MTT (chromogen)
 0.5 mM DMMBQ (electron transfer agent to chromogen)

On this film is deposited a linear gradient containing 0 to 6.0 mM PT+ serving as the hybrid electron transfer agent/electron acceptor. The PT+ is prepared from PT and ferric EDTA.

When the samples of cerebrospinal fluid are added to this device, a blue bar develops that is indicative of the concentration of lactic acid in the cerebrospinal fluid. In this manner different concentrations of lactic acid of 0.2, 0.5, 0.9, 1.0, 1.7 and 2.1 mM were measured. The device has a dynamic range of 0 to 3.0 mM lactic acid.

EXAMPLE 12

An analog to digital colorimetric measurement of choline

Oxygen-free solutions containing 0.30 mM increments of choline, ranging from 2 to 4.1 mM, were added to a series of test tubes containing:
 mM phosphate buffer, pH 7.7-8.8
 3 mM Basic Blue 3 (BB-3) (electron acceptor)
 2 IU choline electron transferase (choline oxidase) (enzyme)

Those reactions containing 2, 2.3, 2.6, and 2.9 mM choline remained a bright blue color; those solutions containing 3.2, 3.5, 3.8, and 4.1 mM choline were rendered colorless. These are in excess of the 3.0 mM threshold concentration.

The experiment is repeated with solutions of choline which were not oxygen-free. Like results are obtained. This serves as further conclusive proof that molecular oxygen, when present, does not participate in the mechanism of the reaction of the present invention.

AA, AC, AB, MB, MG, TH, CB, JGB, BCBA, TOL, RES, GC and PTHF are all acceptable electron acceptors in place of BB3. In all cases, the electron acceptor is colored in the visible spectrum in non-reduced form and is rendered colorless upon reduction.

The electron acceptors are all also capable of accepting electrons directly from the reduced enzyme. This example thus illustrates the system of Embodiment 12 comprising only an enzyme and an electron acceptor without a separate chromogen or electron transfer agent.

EXAMPLE 13

Estimation of semen sample age by measurement of choline concentration

Semen samples and aqueous extracts of dried semen samples are introduced into two-inch long, 40 microliter controlled-volume capillaries, each having a dry film containing:
 2 IU choline electron transferase (choline oxidase) (enzyme)
 2 mM POA (primary electron transfer agent)
 0.2 mM TFBQ (secondary electron transfer agent)
 Buffer On this film is deposited a linear gradient containing 0 to 400 mM ferricyanide electron acceptor.

When semen samples of known or unknown age are added to the devices the enzymatic chemical reaction initiates and the TFBQ transfers electrons from any prematurely reduced MTT to the ferricyanide. A blue bar develops indicative of the concentration of choline in the semen sample. In this manner different concentrations of choline of 20, 50, 90, 100, 160 and 200 mM were measured, indicative of semen samples from 0.6 to 6.0 hours old.

Other organic molecules, for example, glycerin, sorbitol, polyvinyl alcohol and the like can be added to stabilize the enzymes without effect on colorimetric read-out. In addition, inorganic salts such as ammonium sulfate, sodium sulfate and other salts as known in the art can be added to assist in enzyme stability, as can proteins such as ovalbumin and BSA.

Also useful in the practice of the invention ar chemicals that form gels or films that permit storing the essential ingredients in a dry state and rehydrating in the presence of an aqueous solution and controlling color generation. For such known chemicals see U.S. Pat. No. 4,556,634.

The preceding examples can be repeated by substituting or modifying the generically or specifically described components and/or operating conditions of this invention for those used in the preceding examples.

The invention has been described in detail with particular reference to certain preferred embodiments thereof, but it will be understood that variations and modifications can be effected within the spirit and scope of the invention.

We claim:

1. A colorimetric assay system which is designed to measure the presence or concentration of a biochemical analyte in a sample by a color change which is indicative of the presence or concentration of the analyte, wherein the system comprises,
- (a) an oxidase enzyme capable of oxidizing the analyte by removing electrons from the analyte without involving oxygen in the reaction, thereby yielding a reduced enzyme,
- (b) a non-chromogenic electron acceptor which is oxygen, having a half cell reduction potential greater than that of the reduced enzyme, wherein the electron acceptor is capable of accepting electrons from the reduced enzyme in a functionally irreversible manner, and
- (c) a chromogen which is capable of accepting electrons from the reduced enzyme and changing color in a visible range upon reduction, wherein the change of color is less than one equivalent of color per equivalent of analyte oxidized and is indicative of the presence or the concentration of the analyte to be determined.

2. The colorimetric assay system of claim 1 wherein the electron acceptor is capable of directly accepting the electrons from the reduced enzyme in a functionally irreversible manner.

3. The colorimetric assay system of claim 1 wherein the analyte is cholesterol and the enzyme is cholesterol oxidase.

4. The colorimetric assay system of claim 3 wherein the chromogen is Azure B.

5. A colorimetric assay system which is designed to measure the presence or concentration of a biochemical analyte by a color change which is determinative of the presence of concentration of the analyte, wherein the system comprises:
- (a) an oxidase enzyme capable of electron transferase activity with the analyte and capable of oxidizing the analyte by removing electrons from the analyte without involving oxygen in the reaction, thereby yielding a reduced enzyme,
- (b) a chromogen which is capable of accepting electrons derived from the reduced enzyme and is capable of changing color in a visible range upon reduction, the color change of the reduced chromogen being detectable and determinative of the presence or concentration of the analyte to be determined, and
- (c) a non-chromogenic electron acceptor which is not oxygen having a half cell potential greater than the reduced enzyme, which electron acceptor is capable of accepting electrons derived from the reduced enzyme in a functionally irreversible manner, and advantageously competes over any oxygen present to oxidize the reduced enzyme, and
- (d) an electron transfer agent which promotes the transfer of electrons from the reduced enzyme to the electron acceptor, the chromogen, or both.

6. The colorimetric assay system of claim 5 wherein the electron transfer agent is selected from the group consisting of flavins, phenazines, phenothiazines, pheoxazines, indophenols, substituted 1,4-benzoquinones and indamins.

7. The colorimetric assay system of claim 6 wherein the electron transfer agent is a flavin selected from the group consisting of riboflavin, alloxazine and lumichrome.

8. The colorimetric assay system of claim 6 in which the electron transfer agent is a phenothiazine selected from the group consisting of phenothiazine radical cation, thionine, azure A, azure B, azure C, methylene blue, methylene green and toluidine blue.

9. The colorimetric assay system of claim 6 wherein the electron transfer agent is a phenazine selected from the group consisting of phenazine, phenazine methosulfate, phenazine ethosulfate, and safranine.

10. The colorimetric assay system of claim 6 in which the electron transfer agent is a phenothiazine selected from the group consisting of basic blue 3 and brilliant cresyl blue.

11. The colorimetric assay system of claim 6 in which the electron transfer agent is a substituted 1,4-benzoquinone selected from the group consisting of TFBQ, MMBQ, HMBQ, HMMBQ, DMBQ, DMMBQ and CCBQ.

12. The colorimetric assay system of claim 6 in which the electron transfer agent is an indamin selected from the group consisting of Bindschedler's green and phenylene blue.

13. The colorimetric assay system of claim 5 in which the enzyme is cholesterol oxidase and the analyte is cholesterol.

14. The colorimetric assay system of claim 7 in which the electron transfer agent is DCIP.

15. The colorimetric assay system of claim 14 in which the enzyme is choline oxidase and the analyte is choline.

16. The colorimetric assay system of claim 5 in which the electron acceptor competes with the chromogen for electrons from the enzyme, either retarding reduction of the chromogen and thereby causing the color change to be gradual, or preventing reduction of the chromogen until the non-reduced electron acceptor is depleted and an abrupt color change occurs, the intensity of the gradual color change being linearly proportional to the concentration of the analyte, the occurrence of the abrupt color change being determinative of the presence or absence of the analyte below or above a concentration to be determined.

17. The colorimetric assay system of claim 5 wherein the electron transfer agent is phenothiazine, the chromogen is INT and the electron acceptor is ferric chelate.

18. The colorimetric assay system of claim 5 wherein the electron transfer agent is PMS, the chromogen is MTT and the electron acceptor is ferricyanide.

19. The colorimetric assay system of claim 18 in which the enzyme is alcohol oxidase and the analyte is alcohol.

20. The colorimetric assay system of claim 5 wherein the analyte is cholesterol, the enzyme is cholesterol oxidase, the electron transfer agent is selected from the group consisting of phenothiazine radical, phenoxazine, PMS and a substituted 1,4-benzoquinone, the electron acceptor is selected from the group consisting of $K_2IrCl_6$, ferric chelates, ferricyanide, and $NaIO_4$ and the chromogen is a tetrazolium salt compatible with the electron acceptor, and wherein the assay system is analog to digital.

21. The colorimetric assay system of claim 20 wherein the substituted 1,4-benzoquinone electron transfer agent is selected from the group consisting of TFBQ, MMBQ, DMMBQ and CCBQ.

22. The colorimetric assay system of claim 5 wherein the analyte is cholesterol, the enzyme is cholesterol oxidase, the electron transfer agent is selected from the group consisting of phenothiazine radical cation, phenoxazine, phenazine methosulfate and a substituted 1,4- benzoquinone, the electron acceptor is tartrazine, and the chromogen is a tetrazolium salt compatible with the electron acceptor, and wherein the assay system is analog to analog.

23. The colorimetric assay system of claim 5 in which the oxidase is selected from the group consisting of an oxidase requiring a flavin coenzyme and an oxidase containing a pteridine coenzyme.

24. The colorimetric assay system of claim 5 wherein the oxidase contains a reversible oxidizable dithiol group at its active site.

25. The colorimetric assay system of claim 5 wherein the oxidase contains non-heme iron in its reactive center.

26. The colorimetric assay system of claim 5 wherein the electron transfer agent promotes the transfer of electrons to both the chromogen and the electron acceptor.

27. The colorimetric assay system of claim 5 wherein the reduced chromogen has a millimolar extinction coefficient in excess of 10.

28. The colorimetric assay system of claim 5 wherein the electron acceptor is capable of efficient direct interaction with the enzyme and the electron transfer agent promotes the transfer of electrons to the chromogen.

29. The colorimetric assay system of claim 5 wherein the chromogen is capable of efficient direct interaction with the enzyme and the electron transfer agent promotes the transfer of electrons to the electron acceptor.

30. The colorimetric assay system of claim 5 wherein the electron acceptor, the chromogen, or both the electron acceptor and the chromogen are capable of accepting electrons from the reduced enzyme and from electron transfer agent, wherein the electron transfer agent increases the rate of electron transfer, thereby reducing the amount of enzyme needed to achieve a desired rate.

31. The colorimetric assay system of claim 5 wherein the analyte is glucose, and the enzyme is glucose oxidase.

32. The colorimetric assay system of claim 5 wherein the electron transfer agent and the electron acceptor are a hybrid phenothiazine radical cation, and the chromogen is MTT.

33. The colorimetric assay system of claim 32 wherein the phenothiazine radical cation is prepared from phenothiazine and an electron acceptor oxidizing agent selected from the group consisting of $K_2IrCl_6$, $NaIO_4$, and ferric chelates.

34. The colorimetric assay system of claim 33 wherein the ferric chelate is selected from the group consisting of ferricyanide, ferric EDTA, ferric citrate, ferric oxalate, ferric acetylacetonate, ferric bipyridyl, nitroferricyanide and pentacyanoamino ferrate (III).

35. The colorimetric assay system of claim 5 wherein the assay system is analog to analog and wherein the color change is directly proportional to the concentration of analyte to be measured.

36. The colorimetric assay system of claim 35 wherein the electron acceptor is selected from the group consisting of tartrazine, TFBQ, 2,5,-dihydroxy-1,4-benzoquinone and 2-cyclohexyl-5-hydroxy-1,4-benzoquinone and the chromogen is a tetrazolium salt.

37. The colorimetric assay system of claim 35 wherein the biochemical analyte is bilirubin and the enzyme is bilirubin oxidase.

38. The colorimetric assay system of claim 35 wherein the analyte is cholesterol and the enzyme is cholesterol oxidase.

39. The colorimetric assay system of claim 5, further comprising the the biochemical analyte, the presence or concentration of which is to be measured.

40. The colorimetric assay system of claim 39 wherein the analyte is selected from the group consisting of ethanol, methanol, glucose, lactose, galactose, lactate, pyruvate, oxalate, ketones, albumin, triglycerides, cholesterol, bilirubin, hemoglobin, chlorine, oxalic acid, glycerol, lactic acid, pyruvic acid, ascorbic acid and uric acid, and the enzyme is an oxidase capable of oxidizing the analyte.

41. The colorimetric assay system of claim 5 wherein the oxidase is not capable of oxidizing the analyte as initially present, and wherein the assay system further comprises an enzyme or series of enzymes capable of converting the analyte to a product which can be oxidized by the oxidase.

42. The colorimetric assay system of claim 41 wherein the analyte is triglyceride, the enzyme capable of converting the analyte to a product which can be oxidized by the oxidase is a lipase, and the oxidase is glycerol oxidase.

43. The colorimetric assay system of claim 41 wherein the analyte is esterified cholesterol, the enzyme capable of converting the analyte to a product which can be oxidized by the oxidase is an enzyme with cholesterol esterase activity, and the oxidase is cholesterol oxidase.

44. The colorimetric assay system of claim 5 wherein the color change is a change from a colorless state to a colored stat in the visible range.

45. The colorimetric assay system of claim 5 wherein an additional electron transfer agent is added to promote the efficient transfer of electrons from any reduced chromogen to the electron acceptor.

46. The colorimetric assay system of claim 45 wherein the analyte is in a multi-phase composition and the components of the assay system partition differentially between the phases, and the additional electron transfer agent promotes the flow of electrons from reduced chromogen or electron transfer agent in one phase to the electron acceptor in another phase.

47. The colorimetric assay system of claim 46 wherein the multi-phase composition comprises micellar and ionic aqueous phases.

48. The colorimetric assay system of claim 47 wherein the micellar phase comprises lipoprotein particles and the aqueous phase comprises the aqueous component of blood.

49. The colorimetric assay system of claim 45 wherein the electron acceptor/electron transfer agent is a hybrid.

50. The colorimetric assay system of claim 45 wherein the electron transfer agent is phenazine methosulfate, the electron acceptor is ferricyanide, the chromogen is a tetrazolium salt and the electron transfer agent between the chromogen and the electron acceptor is phenoxazine.

51. A colorimetric assay system which is designed to measure the presence or concentration of an oxidase enzyme in a sample by a color change which is indicative of the presence or concentration of the oxidase, wherein the system comprises,
  (a) a substrate which the oxidase is capable of oxidizing by removing electrons from the substrate without involving oxygen in the reaction, wherein the electrons are transferred to an electron acceptor, and wherein the electron acceptor is not oxygen, (b) a non-chromogenic electron acceptor which is not oxygen, having a half cell reduction potential greater than that of the reduced enzyme, wherein the electron acceptor is capable of accepting electrons from the reduced enzyme in a functionally irreversible manner, (c) a chromogen which is capable of accepting electrons from the reduced enzyme and changing color in a visible range upon reduction, wherein the change of color is less than one equivalent of color per equivalent of substrate oxidized and is indicative of the presence or the concentration of the oxidase to be determined, and (d) an electron transfer agent which promotes the transfer of electrons from the reduced enzyme to the electron acceptor, the chromogen, or both the electron acceptor and the chromogen.

52. A diagnostic colorimetric assay device which is designed to measure the concentration of a biochemical analyte in a sample by developing a color signal when the analyte is at or above a threshold concentration and by the absence of a color signal when the concentration of the analyte is below the threshold, wherein the device comprises:

(a) physical support means, (b) an oxidase enzyme capable of oxidizing the analyte by removing electrons from the analyte without involving oxygen in the reaction, thereby yielding a reduced enzyme, (c) a non-chromogenic electron acceptor which is not oxygen, having a half cell reduction potential greater than that of the reduced enzyme, wherein the electron acceptor is capable of accepting electrons from the reduced enzyme in a functionally irreversible manner, (d) a chromogen which is capable of accepting electrons from the reduced enzyme and changing color in a visible range upon reduction, wherein the change of color is less than one equivalent of color per equivalent of analyte oxidized and is indicative of the concentration of the analyte to be determined, and (e) an electron transfer agent which promotes the transfer of electrons from the reduced enzyme to the electron acceptor, the chromogen, or both the electron acceptor and the chromogen.

53. The device of claim 52 wherein the physical support means is a multi-layer dry film or gel situated inside a controlled volume capillary.

54. The device of claim 52 which further comprises a sampling means.

55. The device of claim 54 wherein the sampling means is a lancet for sampling blood.

56. A method for measuring the presence or the concentration of a biochemical analyte in a sample by the development of a color change wherein the method comprises:

(a) contacting the sample with an assay system comprising (i) an oxidase enzyme capable of oxidizing the analyte by removing electrons from the analyte without involving oxygen in the reaction, thereby yielding a reduced enzyme, (ii) a non-chromogenic electron acceptor which is not oxygen, having a half cell reduction potential greater than that of the reduced enzyme, wherein the electron acceptor is capable of accepting electrons from the reduced enzyme in a functionally irreversible manner, (iii) a chromogen which is capable of accepting electrons from the reduced enzyme and changing color in a visible range upon reduction, wherein the change of color is less than one equivalent of color per equivalent of analyte oxidized and is indicative of the concentration of the analyte to be determined, and (iv) an electron transfer agent which promotes the transfer of electrons from the reduced enzyme to the electron acceptor, the chromogen, or both the electron acceptor and the chromogen, (b) incubating to permit oxidation of the analyte, and (c) detecting a color change resulting from reduction of the chromogen, wherein a visible color change is indicative of the presence of the analyte or a concentration of the analyte above a predetermined threshold and wherein the absence of a visible color change is indicative of the absence of the analyte or a concentration of the analyte below a predetermined threshold.

57. A method for measuring the presence or the concentration of an oxidase enzyme in a sample by the development of a color change wherein the color change is indicative of the presence or concentration of the oxidase, wherein the method comprises:

(a) contacting the sample with an assay system comprising (i) a substrate which the oxidase is capable of oxidizing by removing electrons from the substrate without involving oxygen in the reaction, wherein the electrons are transferred to an electron acceptor, and wherein the electron acceptor is not oxygen, (ii) a non-chromogenic electron acceptor which is not oxygen, having a half cell reduction potential greater than that of the reduced enzyme, wherein the electron acceptor is capable of accepting electrons from the reduced enzyme in a functionally irreversible manner, (iii) a chromogen which is capable of accepting electrons from the reduced enzyme and changing color in a visible range upon reduction, wherein the change of color is less than one equivalent of color per equivalent of substrate oxidized and is indicative of the concentration of the substrate to be determined, and (iv) an electron transfer agent which promotes the transfer of electrons from the reduced enzyme to the electron acceptor, the chromogen, or both the electron acceptor and the chromogen, (b) incubating to permit the oxidation of the substrate, and (c) detecting a color change resulting from reduction of the chromogen, wherein a visible color change is indicative of the presence of the oxidase or a concentration of the oxidase above a predetermined threshold and wherein the absence of a visible color change is indicative of the absence of the oxidase or a concentration of the oxidase below a predetermined threshold.

58. The colorimetric assay system of claim 39, further comprising a reactant which reacts with the analyte to convert the analyte to a product in situ, and an oxidase capable of oxidizing the product.

59. The colorimetric assay system of claim 49 wherein the electron acceptor/electron transfer agent hybrid is phenothiazine radical cation, the electron transfer agent between the enzyme and the chromogen is DMMBQ, and the electron transfer agent between the chromogen and the electron acceptor is TFBQ.

60. A colorimetric assay system which is designed to measure the presence or concentration of a biochemical analyte in a sample by a color change which is determinative of the presence or concentration of the analyte, which system comprises:

(a) a heme- or copper-containing protein capable of oxidizing the analyte by removing electrons from the analyte without involving oxygen in the reaction thereby yielding a reduced protein, (b) a chromogen which is capable of accepting electrons from the reduced protein and is capable of changing color in a visible range upon reduction, the change of the reduced chromogen being detectable and determinative of the presence or concentration of the analyte to be determined, and (c) a non-chromogenic electron acceptor which is not oxygen, having a half cell potential greater than the reduced enzyme, wherein the electron acceptor is capable of accepting electrons from the reduced enzyme in a functionally irreversible manner, and (d) an electron transfer agent which promotes the transfer of electrons from the reduced enzyme to the electron acceptor, the chromogen, or both.

61. The colorimetric assay system of claim 60, wherein the heme- or copper-containing protein is selected from the group consisting of serum monoamine oxidase, liver dopamine hydroxylase, hemocyanin, laccase, uricase, phenolase, transsulferase, cerebrocuprein, erythrocyprein, hepatocuprein, plastocyanin, dopamine-2-hydroxylase, liver aryl-4-hydroxylase, liver naphthalene hydroxylase, alkoxyaryl hydroxylase and fatty acid desaturase.

* * * * *

UNITED STATES PATENT AND TRADEMARK OFFICE
CERTIFICATE OF CORRECTION

PATENT NO. : 5,126,247

DATED : June 30, 1992

INVENTOR(S) : John L. Palmer, James B. Johnston, Marsha W. Timmerman

It is certified that error appears in the above-identified patent and that said Letters Patent is hereby corrected as shown below:

```
Claim 1, column 39, line 9, before "oxygen" insert --not--.
Claim 6, column 39, line 60, "pheoxazines" should read --phenoxazines--.
Claim 10, column 40, line 8, "phenothiazine" should read --phenoxazine--.
Claim 44, column 42, line 31, "stat" should read --state--.
Claim 52, column 43, line 32, before "oxygen" insert --not--.
Claim 56, column 43, line 66, before "oxygen" insert --not--.
Claim 60, column 45, line 20, before "change" insert --color--.
```

Signed and Sealed this

Twenty-eighth Day of September, 1993

Attest:

Attesting Officer

BRUCE LEHMAN

Commissioner of Patents and Trademarks